US006972168B2

(12) United States Patent
Muir

(10) Patent No.: US 6,972,168 B2
(45) Date of Patent: Dec. 6, 2005

(54) MATERIALS AND METHODS FOR NERVE GRAFTING, SELECTION OF NERVE GRAFTS, AND IN VITRO NERVE TISSUE CULTURE

(75) Inventor: David F. Muir, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 10/218,864

(22) Filed: Aug. 13, 2002

(65) Prior Publication Data

US 2003/0040112 A1 Feb. 27, 2003

Related U.S. Application Data

(60) Provisional application No. 60/311,870, filed on Aug. 13, 2001.

(51) Int. Cl.$^7$ .......................... A01N 1/00; A01N 1/02; C12N 5/06; C12N 5/08
(52) U.S. Cl. ...................................... 435/1.1; 435/368
(58) Field of Search .................................. 435/1.1, 368

(56) References Cited

U.S. PATENT DOCUMENTS

| | | | |
|---|---|---|---|
| 4,696,816 A | 9/1987 | Brown | |
| 4,933,185 A | 6/1990 | Wheatley et al. | |
| 5,231,580 A | 7/1993 | Cheung et al. | |
| 5,292,509 A | 3/1994 | Hageman | |
| 5,716,617 A | 2/1998 | Khandke et al. | |
| 5,830,468 A | 11/1998 | Bini | |
| 5,866,120 A | 2/1999 | Karageozian et al. | |
| 5,916,557 A | 6/1999 | Berlowitz-Tarrant et al. | |
| 5,997,863 A | 12/1999 | Zimmermann et al. | |
| 6,033,660 A * | 3/2000 | Mather et al. | 424/93.7 |
| 6,054,569 A | 4/2000 | Bennett et al. | |
| 6,093,563 A | 7/2000 | Bennett et al. | |
| 6,200,564 B1 | 3/2001 | Lamont et al. | |
| 6,214,978 B1 | 4/2001 | Truog et al. | |
| 6,231,608 B1 * | 5/2001 | Stone | 623/16.11 |
| 6,267,786 B1 | 7/2001 | Stone | |
| 6,448,076 B2 * | 9/2002 | Dennis et al. | 435/325 |
| 6,455,309 B2 | 9/2002 | Stone | |
| 2001/0034043 A1 | 10/2001 | Su et al. | |
| 2001/0039459 A1 | 11/2001 | Stone | |
| 2003/0068815 A1 | 4/2003 | Stone et al. | |
| 2003/0072749 A1 | 4/2003 | Muir | |
| 2003/0077258 A1 | 4/2003 | Muir | |

FOREIGN PATENT DOCUMENTS

| | | |
|---|---|---|
| DE | 19530556 | 9/1996 |
| EP | 0 576 294 A2 | 12/1993 |
| EP | 0 613 949 A2 | 9/1994 |
| EP | 0 776 968 A1 | 6/1997 |
| EP | 0 875 253 A2 | 11/1998 |
| WO | WO 91/06303 A1 | 5/1991 |
| WO | WO 91/06573 A1 | 5/1991 |
| WO | WO 01/35977 A2 | 5/2001 |
| WO | WO 01/39795 A2 | 6/2001 |
| WO | 2003/015612 A3 | 2/2003 |

OTHER PUBLICATIONS

Evans et al. Progress in Neurobiology, 1994. vol. 43, pp. 187-233.*
Lassner et al. Journal of Reconstructive Microsurgery. Nov. 1995. vol. 11, No. 6, pp. 447-453.*
Ferguson et al. Molecular and Cellular Neuroscience. 2000. 16: 157-167.*
Krekoski, C.A. et al. "Metalloproteinase-Dependent Predegeneration In Vitro Enhances Axonal Regeneration within Acellular Peripheral Nerve Grafts" *J. Neuroscience*, Dec. 2002, 22(23):10408-10415.
Lemons, M.L. et al. "Chondroitin Sulfate Proteoglycan Immunoreactivity Increases Following Spinal Cord Injury and Transplantation" *Exper. Neuro.*, 1999, 160:51-65.
McKeon, R.J. et al. "Reduction of Neurite Outgrowth in a Model of Glial Scarring following CNS Injury is Correlated with the Expression of Inhibitory Molecules on Reactive Astrocytes" *J. Neurosci.*, 1991, 11(11):3398-3411.
McKeon, R.J. et al. "Injury-Induced Proteoglycans Inhibit the Potential for Laminin-Mediated Axon Growth on Astrocytic Scars" *Exp. Neuro.*, 1995, 136:32-43.
Yick, L-W. et al. "Chondroitinase ABC promotes axonal regeneration of Clarke's neurons after spinal cord injury" *NeuroReport*, 2000, 11(5):1063-1067.
Jones, L.L. et al. "Neurotrophic factors, cellular bridges and gene therapy for spinal cord injury" *J. Physiology*, 2001, 533. 1:83-89.
Smith-Thomas, L.C. et al. "Increased axon regeneration in astrocytes grown in the presence of proteoglycan synthesis inhibitors" *J. Cell Sci.*, 1995, 108:1307-1315.
Smith-Thomas, L.C. et al. "An inhibitor of neurite outgrowth produced by astrocytes" *J. Cell Sci.*, 1994 107: 1687-1695.
Bradbury, E.J. et al. "Chondroitinase ABC promotes functional recovery after spinal cord injury" *Nature*, Apr. 2002, 416(6881):636-640.
Muir, D. et al. "Schwannoma Cell-derived Inhibitor of the Neurite-promoting activity of Laminin" *J. Cell Biol.*, Nov. 1989, 109:2353-2362.

(Continued)

*Primary Examiner*—Vera Afremova
(74) *Attorney, Agent, or Firm*—Goodwin Procter LLP

(57) ABSTRACT

The subject invention pertains to compositions and methods for culturing nerve tissue in vitro and nerve grafts produced using such methods. The compositions and methods of the subject invention can be employed to restore the continuity of nerve interrupted by disease, traumatic events or surgical procedures. The invention also concerns methods for promoting repair of damaged nerve tissue using the present compositions and nerve tissue treated according to such methods.

46 Claims, 15 Drawing Sheets

OTHER PUBLICATIONS

Bennett, G.S. et al. "Chondroitinase ABC delivered to the site of a spinal cord injury upregulates GAP-43 expression in dorsal root ganglion neurons" *Society for Neuroscience Abstracts*, 2000, 26(1-2):Abstract No. 324.3 from 30th Annual Meeting of the Society of Neuroscience, presented Nov., 2000; mailed to subscribers Sep., 2000.

Schmalfeldt et al., "Brain Derived Versican V2 is a Potent Inhibitor of Axonal Growth," *Journal of Cell Science* 113: 807-816 (2000).

Braunewell, K-H. et al. "Functional Involvement of Sciatic Nerve-derived Versican- and Decorin-like Molecules and other Chondroitin Sulphate Proteoglycans in ECM-mediated Cell Adhesion and Neurite Outgrowth" *Euro. J. Neurosci.*, 1995, 7:805-814.

Braunewell, K-H. et al. "Up-regulation of a Chondroitin Sulphate Eptiope during Regeneration of Mouse Sciatic Nerve: Evidence that the Immunoreactive Molecules are Related to the Chondroitin Sulphate Proteogylcans Decorin and Versican" *Eur J. Neurosci*, 1995, 7:792-804.

Brown, M.C. et al. "Further Studies on Motor and Sensory Nerve Regeneration in Mice With Delayed Wallerian Degeneration" *Eur J Neurosci*, 1994, 6:420-428.

Evans, P.J. et al. "Regeneration Across Cold Preserved Peripheral Nerve Allografts" *Microsurgery*, 1999, 19:115-127.

Hasan, N. et al. "The influence of predegenerated nerve grafts on axonal regeneration from prelesioned peripheral nerves" *J Anat*, 1996, 189:293-302.

Lassner, F. et al. "Preservation of Peripheral Nerve Grafts: A Comparison of Normal Saline, HTK Organ Preservation Solution, and DMEM Schwann Cell Culture Medium" *J Reconstr Microsurg*, 1995, 11:447-453.

Nadim, W. et al. "The role of Schwann cells and basal lamina tubes in the regeneration of axons through long lengths of freeze-killed nerve grafts" *Neuropathol Appl Neurobiol*, 1990, 16:411-421.

Stoll, G. and H.W. Müller "Nerve Injury, Axonal Degeneration and Neural Regeneration: Basic Insights" *Brain Pathology*, 1999, 9:313-325.

Agius, E. and P. Cochard "Comparison of Neurite Outgrowth Induced by Intact and Injured Sciatic Nerves: A Confocal and Functional Analysis" *The Journal of Neuroscience*, Jan. 1, 1998, 18(1):328-338.

Bertolotto, A. et al. "Immunohistochemical Localizationof Chondroitin Sulfate in Normal and Pathological Human Muscle" *J Neurol Sci*, 1986, 73:233-244.

Bradbury, E.J. et al. "Chondroitinase ABC Delivered to the Site of a Spinal Cord Injury Upregulates GAP-43 Expression in Dorsal Root Ganglion Neurons" *Soc. Neurosci Abstr*, Nov. 2000, abstract presented at the 30th Annual Meeting of the Society of Neuroscience.

Danielsen, N. et al. "Predegeneration enhances regeneration into acellular nerve grafts" *Brain Res*, 1995, 681:105-108.

Danielsen, N. et al. "Pre-degenerated nerve grafts enhance regeneration by shortening the initial delay period" *Brain Res*, 1994, 666:250-254.

Evans, P.J. et al. "The Peripheral Nerve Allograft: A Comprehensive Review of Regeneration and Neuroimmunology" *Prog Neurobiol*, 1994, 43:187-233.

Evans, P.J. et al. "Cold Preserved Nerve Allografts: Changes in Basement Membrane, Viability, Immunogenicity, and Regeneration" *Muscle Nerve*, Nov. 1998, 21:1507-1522.

Fawcett, J.W. and R.J. Keynes "Peripheral Nerve Regeneration" *Annu Rev Neurosci*, 1990, 13:43-60.

Ferguson, T.A. and D. Muir "MMP-2 and MMP-9 Increase the Neurite-Promoting Potential of Schwann Cell Basal Laminae and Are Upregulated in Degenerated Nerve" *Mol Cell Neurosci*, 2000 16:157-167.

Fu, S.Y. and T. Gordon "The Cellular and Molecular Basis of Peripheral Nerve Regeneration" *Mol Neurobiol*, 1997, 14(1):67-116.

Giannini, C. and P. Dyck "The Fate of Schwann Cell Basement Membranes in Permanently Transected Nerves" *J Neuropathol Exp Neurol*, 1990 49(6):550-563.

Gordon, L. et al. "Predegenerated nerve autografts as compared with fresh nerve autografts in freshly cut and precut motor nerve defects in the rat" *J Hand Surg [Am]*, Jan. 1979, 4(1):42-47.

Gulati, A.K. "Evaluation of acellular and cellular nerve grafts in repair of rat peripheral nerve" *J Neurosug*, Jan. 1988, 68:117-123.

Ide, C. et al. "Schwann Cell Basal Lamina and Nerve Regeneration" *Brain Res*, 1983, 288:61-75.

Kherif, S. et al. "Matrix metalloproteinases MMP-2 and MMP-9 in denervated muscle and injured nerve" *Neuropathol Appl Neurobiol*, 1998, 24:309-319.

Krekoski, C.A. et al. "Axonal Regeneration into Acellular Nerve Grafts Is Enhanced by Degradation of Chondroitin Sulfate Proteoglycan" *The Journal of Neuroscience*, Aug. 15, 2001, 21(16):6206-6213.

La Fleur, M. et al. "Basement Membrane and Repair of Injury to Peripheral Nerve: Defining a Potential Role for Macrophages, Matrix Metalloproteinases, and Tissue Inhibitor of Metalloproteinases-1" *J. Exp. Med.*, Dec. 1996, 184: 2311-2326.

Langley, J.N. and H.K. Anderson "The Union of Different Kinds of Nerve Fibres" *J Physiol*, 1904, 31:365-391.

Levi, A. et al. "Cold Storage of Peripheral Nerves: An In Vitro Assay of Cell Viability and Function" *Glia*, 1994, 10:121-131.

Moon, L. et al. "Regeneration of CNS axons back to their target following treatment of adult rat brain with chondroitinase ABC" *Nature Neuroscience*, May 2001, 4 (5):465-466.

Muir, D.F. "Enzymatic De-Inhibition of Axonal Regeneration", Abstract, Grant No. 1R01NS037901-01A1, Computer Retrieval of Information on Scientific Projects (CRISP) database, http://crisp.cit.nih.gov/, maintained by the Office of Extramural Research at the National Institutes of Heath (NIH), Apr. 2, 2001.

Ochi, M. et al. "Nerve Regeneration in Predegenerated Basal Lamina Graft: The Effect of Duration of Predegeneration on Axonal Extension" *Exp Neurol*, 1994, 128:216-225.

Olmarker, K. et al. "Chondroitinase ABC (Phamaceutical Grade) for Chemonucleolysis" *Spine*, 1996, 21:1952-1956.

Salonen, V. et al. "Laminin in traumatized peripheral nerve: basement membrane changes during degeneration and regeneration" *J Neurocytol*, 1987, 16:713-720.

Shubayev, V.I. and R.R. Myers "Upregulation and interaction of TNFα and gelatinases A and B in painful peripheral nerve injury" *Brain Res*. 2000, 855:83-89.

Siebert, H. et al. "Matrix Metalloproteinase Expression and Inhibition After Sciatic Nerve Axotomy" *J Neuropathol Exp Neurol*, Jan. 2001, 60(1):85-93.

Strasberg, S.R. et al. "Peripheral Nerve Allograft Preservation Improves Regeneration and Decreases Systemic Cyclosporin A Requirements" *Experimental Neurology*, 1996, 139:306-316.

Taskinen, H.S. and M. Röyttä "The dynamics of macrophage recruitment after nerve transection" *Acta Neuropathol* (Berl), 1997, 93:252-259.

Tkalec, A.L. et al. "Isolation and Expression in *Escherichia coli* of cslA and cslB, Genes Coding for the Chondroitin Sulfate-Degrading Enzymes Chondroitinase AC and Chondroitinase B, Respectively, from *Flavobacterium heparinum*" *Appl. Environ. Microbiol.*, Jan. 2000, 66(1):29-35.

Wang, G-Y. et al. "The role of laminin, a component of Schwann cell basal lamina, in rat sciatic nerve regernation within antiserum-treated nerve grafts" *Brain Res*, 1992, 570:116-125.

Yamada, T. et al. "Selective localization of gelatinase A, an enzyme degrading β-amyloid protein, in white matter microglia and in Schwann cells" *Acta Neuropathol* (Berl), 1995, 89:199-203.

Zuo, J. et al. "Degradation of Chondroitin Sulfate Proteoglycan Enhances the Neurite-Promoting Potential of Spinal Cord Tissue" *Exp Neurol*, 1998, 154:654-662.

Zuo, J. et al. "Chondroitin Sulfate Proteoglycan with Neurite-Inhibiting Activity Is Up-regulated following Peripheral Nerve Injury" *J Neurobiol*, 1998, 34:41-54.

Zuo, J. et al. "Neuronal Matrix Metalloproteinase-2 Degrades and Inactivates a Neurite-Inhibiting Chondroitin Sulfate Proteoglycan" *The Journal of Neuroscience*, Jul. 15, 1998, 18(4):5203-5211.

Zuo, J. et al. "Regeneration of Axons after Nerve Transection Repair Is Enhanced by Degradation of Chondroitin Sulfate Proteoglycan" *Exp. Neurology*, 2002, 176:221-228.

* cited by examiner

FIG. 1A
FIG. 1B
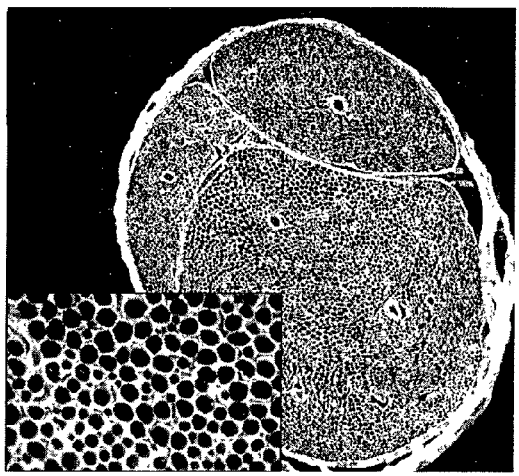
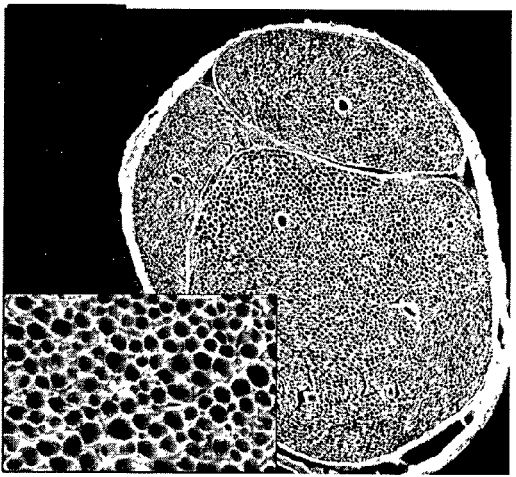
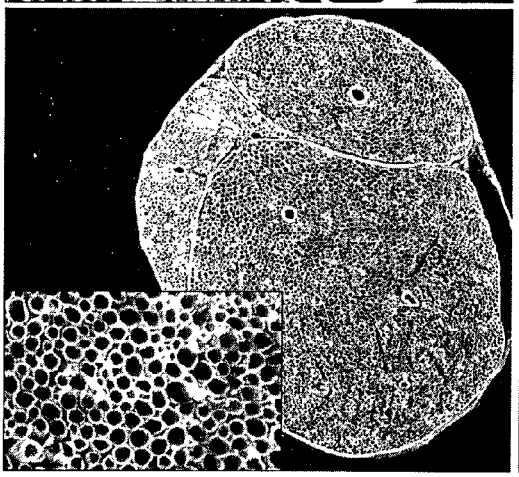
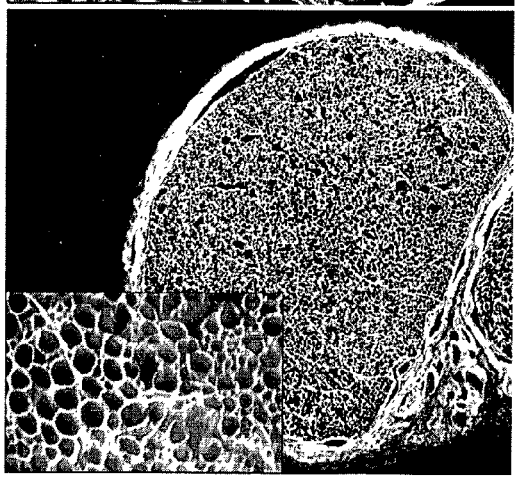
FIG. 1C
FIG. 1D

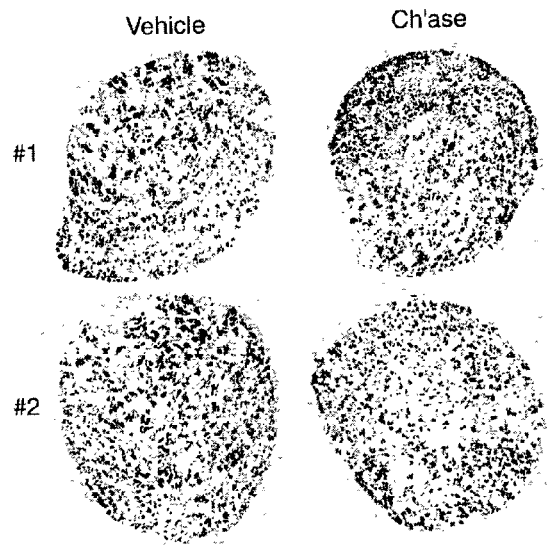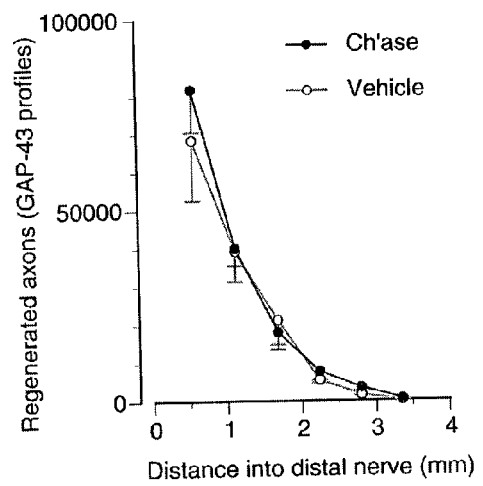
FIG. 13A
FIG. 13B
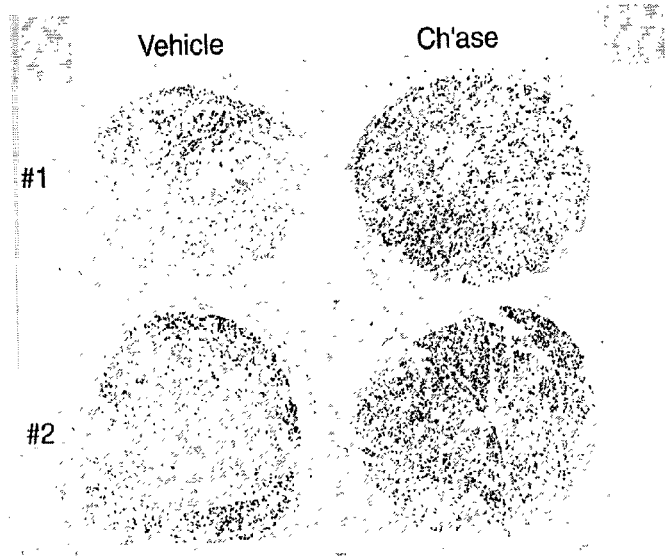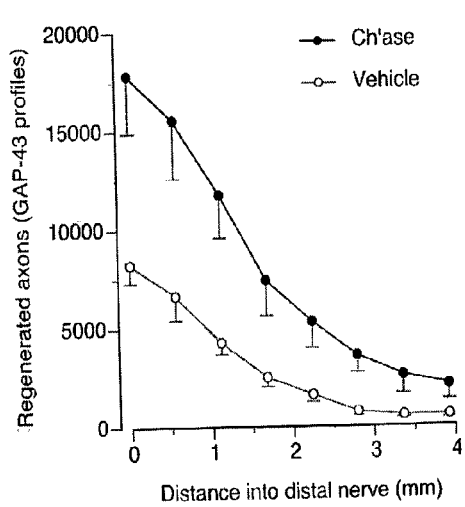
FIG. 14C
FIG. 14D

MATERIALS AND METHODS FOR NERVE GRAFTING, SELECTION OF NERVE GRAFTS, AND IN VITRO NERVE TISSUE CULTURE

CROSS-REFERENCE TO RELATED APPLICATION

This application claims the benefit of provisional patent application Ser. No. 60/311,870, filed Aug. 13, 2001, which is hereby incorporated by reference in its entirety, including all figures, tables, and drawings.

The subject invention was made with government support under a research project supported by National Institutes of Health Grant No. R01 NS37901. The government has certain rights in this invention.

BACKGROUND OF THE INVENTION

Peripheral nerve injuries are a major source of chronic disability. Poor management of nerve injuries is associated with muscle atrophy and can lead to painful neuroma when severed axons are unable to reestablish continuity with the distal nerve. Although nerves have the potential to regenerate after injury, this ability is strictly dependent upon the regenerating nerve fibers (and their axonal sprouts) making appropriate contact with the severed nerve segment (and the Schwann cell basal laminae therein). Regenerating axons that fail to traverse the gap or injury site and enter the basal lamina of the severed distal nerve segment will deteriorate, resulting in neuronal death, muscle atrophy and permanent functional deficit (Fawcett J W et al. [1990] *Annu Rev Neurosci* 13:43–60).

Briefly, a nerve carries the peripheral processes (or axons) of neurons. The neuronal cell bodies reside in the spinal cord (motor neurons), in ganglia situated along the vertebral column (spinal sensory ganglia) or in ganglia found throughout the organs of the body (autonomic and enteric ganglia). A nerve consists of axons, Schwann cells and extensive connective tissue sheaths (Dagum AB [1998] *J Hand Ther* 11:111–117). The outer covering, the epineurium, is made of collagenous connective tissue that cushions the fascicles from external pressure and surrounds the perineunrum. The perineurium surrounds the individual fascicles and, together with endothelial cells in the endoneurial microvessels, functions as the blood-nerve barrier. The endoneurium lies inside the perineurium and consists of collagenous tissue that surrounds the Schwann cells and axons. A fascicular group consists of two or more fascicles surrounded, respectively, by perineurium and epineurium. The topography of nerves is constant distally, with a group of fascicles being either sensory or motor. The neuron consists of a soma (cell body) and an axon, which can be several feet long.

In nerve injuries where there is axonal disruption, but the continuity of the endoneurial sheath remains intact (e.g., crush injury), axons regenerate within their original basal lamina and complete recovery can be expected. In contrast, axonal regrowth may be severely compromised after nerve transection and surgical repair is highly dependent on the realignment of the nerve elements described above (Dagum A B [1998] *J Hand Ther* 11:111–117). Epineurial coaptation (neurorrhaphy) is the primary method of dealing with nerve transection. However, the extent of regeneration is highly variable and, at best, partial recovery of function can be expected (Terzis J K et al. [1990] The Peripheral Nerve: Structure, function and reconstruction, Hampton Press, Norfolk). Full restoration of function after repair of nerve transection remains an unobtainable ideal because of the fine microstructure of nerves and an inability to achieve precise axon-to-axon coaptation, despite the current state of the art in microsurgical techniques.

Nerve grafting is warranted with nerve ablation but presents several practical challenges. Over the years, various nerve graft alternatives have been explored. Presently viewed as a developing alternative is the application of allogenic nerve grafts. While the availability of donor grafts suffers the difficulties of other organ replacement strategies, the importance of viable cellular elements in nerve grafts may be far less important. Although Schwann cells contribute significantly to the regenerative process, the nerve sheath structure contains the essential scaffolding and adhesive cues to promote axonal regeneration and significant regeneration has been achieved in acellular (e.g., freeze-killed) nerve grafts (Ide C et al. [1983] *Brain Res* 288:61–75; Hall S M [1986] *Neuropathol Appl Neurobiol* 12:401–414; Gulati A K [1988] *J Neurosurg* 68:117–123; Nadim W et al. [1990] *Neuropathol Appl Neurobiol* 16:411–421). Killing the resident antigen-presenting cells (e.g., Schwann cells, fibroblasts, endothelial cells, etc.) greatly reduces the immunogenicity of the graft. Use of acellular nerve grafts greatly reduces or eliminates the concerns of host-graft immunorejection (Evans P J et al. [1994] *Prog Neurobiol* 43:187–233; Evans P J et al. [1998] *Muscle Nerve* 21:1507–1522). These features provide considerable promise for the use of freeze-killed (acellular) allogenic and xenogenic nerve grafts. On the other hand, the absence of viable cells precludes nerve degeneration and subsequent remodeling which seem to promote the regenerative process (Bedi K S et al. [1992] *Eur J Neurosci* 4:193–200; Danielsen N et al. [1994] *Brain Res* 666:250–254).

Laminin is a major growth-promoting component of the basal lamina that represents the adhesive stimulus for successful axonal regeneration (Wang, G Y et al. [1992] *Brain Res* 570:116–125). However, while normal (uninjured) nerve is rich in laminin, normal nerve remains inhibitive or refractory to axonal growth. (Langley J N [1904] *J Physiol* 31:365–391; Brown M C et al. [1994] *Eur J Neurosci* 6:420–428). This suggests that the growth-promoting activity of laminin is suppressed in a normal nerve environment and that laminin activity must somehow be revived in nerve degeneration and ensuing regeneration.

Normal peripheral nerve is a poor substratum for axonal growth (Zuo J. et al. [1998] *J Neurobiol* 34: 41–54; Bedi K S et al. [1992] *Eur J Neurosci* 4: 193–200). Experimental results indicate that laminin within normal nerve basal laminae is not accessible to regenerating axon sprouts (Zuo J. et al. [1998] *J Neurosci* 18: 5203–5211; Ferguson T A, and D. Muir [2000] *Mol Cell Neurosci* 16: 157–167; Agius E. et al. [1998] *J Neurosci* 18: 328–338). Upon injury to the nerve, the severed segment (distal to the injury) undergoes an extensive degenerative process that initiates extensive remodeling. In injury-induced nerve degeneration, the severed axons die, their myelin sheath fragments and the resulting debris are removed by phagocytosis. Despite this degeneration, the sheath structures and basal lamina are preserved. The Schwann cells proliferate and prepare the nerve for the regrowth of axons. This entire process, including the remodeling aspect, is generally referred to as nerve degeneration. It is now clear that nerve injury results in positive modifications to the distal nerve segment and experiments show that degenerated nerve has greater axon growth-promoting potential than normal nerve (Bedi K S et al. [1992] *Eur J Neurosci* 4: 193–200; Danielsen N J et al. [1994] *Brain Res* 666: 250–254; Agius E et al. [1998] *J*

*Neurosci* 18: 328–338). Therefore, the degenerative process appears to involve mechanisms that convert normal nerve from a suppressed state to one that promotes axonal growth (Salonen V J et al. [1987] *J Neurocytol* 16: 713–720; Danielsen N et al. [1995] *Brain Res* 681: 105–108).

Loss of function associated with nerve injury results from axon disruption. Axons are very thin and fragile and the slightest injury (including compression) can cause a severing response (axotomy). In axotomy the axon distal to the lesion dies and degenerates. The least problematic injury to a nerve is a crush injury (axonotmesis), where there is axotomy but the continuity of the nerve sheaths remains intact. In the case of axonotmesis, axons typically regenerate without surgical intervention because the basal laminae remain continuous. For severed peripheral nerves to regenerate successfully, axonal sprouts emanating from the proximal nerve stump first must locate and then access Schwann cell basal laminae in the distal nerve segment. This decisive requirement is thought to contribute to the relatively poor regeneration achieved after nerve transection as compared to crush injury. In nerve transection (neurotmesis) the nerve is partially or fully severed. Transection injuries are those in which both axons and the nerve sheaths are severed, disrupting the continuity of the nerve and the guidance mechanisms required for axon regeneration. Surgical coaptation (neurorrhaphy) to re-establish the continuity of nerve elements of the nerve is essential for regrowth of axons. In addition, axonal regrowth after nerve transection and repair is further complicated by the misalignment of proximal and distal elements. Even in the instances of clean transection by a sharp instrument, the entire nerve structure is disrupted. Swelling and axoplasmic outflow from the cut ends causes a mushrooming effect which interferes with accurate coaptation and realignment of the basal lamina scaffolding. Despite improvements in fascicular alignment achieved by microsurgical technique, axon-to-axon coaptation remains an idealistic goal. Because of the small size of axons and the relative preponderance of connective tissues, the majority of axonal sprouts emerging from the proximal stump after surgical coaptation are most likely to first encounter a nonpermissive substratum rich in inhibitory chondroitin sulfate proteoglycan (CSPG). This may explain the significant latency and erratic regeneration associated with peripheral nerve transection repair. Evidence indicates that CSPGs bind to and inhibit the growth-promoting activity of laminin and that CSPG is degraded during the degenerative process after injury. Accordingly, the process by which CSPGs are inactivated can explain why regeneration is essential for nerve regeneration. It has recently been found that peripheral nerve contains abundant CSPG, which inhibits the growth-promoting activity of endoneurial laminin (Zuo J et al. [1998a] *J Neurobiol* 34:41–54). The neurite-inhibiting CSPGs are abundant in the endoneurial tissues surrounding Schwann cell basal laminae and are rapidly upregulated after nerve injury (Braunewell K H et al. [1995a] *Eur J Neurosci* 7:805–814; Braunewell K H et al. [1995b] *Eur J Neurosci* 7:792–804). Consequently, any misalignment of nerve microstructure (after injury and repair) forces regenerating axonal sprouts to negotiate nonpermissive tissues which may severely limit their access to basal laminae in the distal nerve. Recent research supports the conclusion that certain CSPG-degrading enzymes represent a mechanism by which the growth-promoting properties of laminin may be restored within degenerating nerve (Zuo J et al. [1998b] *J Neurosci* 18:5203–5211; Ferguson T A et al. [2000] *Mol Cell Neurosci* 16:157–167). In addition, this process can be achieved by the application of CSPG-degrading enzymes at the site of nerve injury and to nerve grafts to improve regeneration (Zuo J et al. [2002] *Exp Neurol* 176: 221–228; Krekoski C A et al. [2001] *J Neurosci* 21: 6206–6213). One such CSPG-degrading enzyme that is particularly effective is chondroitinase ABC, a bacterial enzyme that degrades the disaccharide side-chains of CSPG (Zuo J et al. [1998a] *J Neurobiol* 34:41–54). Other include specific members of the matrix metalloproteinase family, MMP-2 and MMP-9, that degrade the core protein of CSPG (Ferguson T A et al. [2000] *Mol Cell Neurosci* 16: 157–167).

Although chondroitinase ABC (a glycosaminoglycan lyase) degrades chondroitin sulfate, dermatan sulfate and hyaluronan, its ability to enhance the growth-promoting property of nervous tissue has been attributed to CSPG degradation (Zuo J et al. [1998] *Exp Neurol* 154:654–662; Ferguson T A et al. [2000] *Mol Cell Neurosci* 16:157–167). In addition, it has been shown that chondroitinase ABC treatment does not disrupt nerve sheath organization or displace laminin from the Schwann cell basal lamina (Krekoski C A et al. [2001] *J Neurosci* 21:6206–6213).

In nerve transection repair models, degradation of inhibitory CSPG removed a major obstacle to regenerating axonal sprouts and resulted in more robust and uniform growth into the distal nerve (Krekoski C A et al. [2001] *J Neurosci* 21:6206–6213).

It has been shown that degenerated nerve has an increased ability to support axonal growth (Giannini C et al. [1990] *J Neuropathol Exp Neurol* 49:550–563; Hasan N et al. [1996] *J Anat* 189:293–302). The effects of degeneration are likely due to modifications of the nerve basal lamina since axonal regeneration is also improved into acellular grafts prepared from predegenerated nerve (Danielsen N et al. [1995] *Brain Res* 681:105–108). Throughout the degenerative process, the Schwann cell basal lamina remains structurally intact.

Animal models have shown that grafts made from nerves that are predegenerated in vivo are much better at supporting nerve regeneration than freshly-cut grafts (Danielsen N et al. [1995] *Brain Res* 681:105–108). However, the procedure for creating pre-degenerated nerves in humans is impractical (i.e., nerve injury followed by a period of survival in vivo to allow tissue degeneration).

Peripheral nerve degeneration in vivo results in an increased turnover of several extracellular matrix molecules which depends on the release and activation of proteolytic enzymes by neurons, Schwann cells and invading macrophages. Modulation of matrix metalloproteinase (MMP) activities after injury implicates MMP-2 and MMP-9 in remodeling of the extracellular matrix during nerve degeneration and regeneration (La Fleur et al. [1996] *J Exp Med* 184: 2311–2326; Kherif et al. [1998] *Neuropathol Appl Neurobiol* 24:309–319; Ferguson et al. [2000] *Mol Cell Neurosci* 16:157–167). MMP-9 is expressed in the peripheral nerve immediately after injury and mainly at the site of injury. MMP-9 expression correlates with the breakdown of the blood-nerve barrier, the accumulation of granulocytes and the invasion of macrophages (Shubayev et al. [2000] *Brain Res* 855:83–89; Siebert et al. [2001] *J Neuropathol Exp Neurol* 60:85–93). Most evidence suggests that hematogenic cells contribute significantly to the elevation of MMP-9 activity (Taskinen et al. [1997] *Acta Neuropathol* (Berl) 93:252–259). On the other hand, MMP-2 is expressed constitutively by Schwann cells in normal peripheral nerve (Yamada et al. [1995] *Acta Neuropathol* (Berl) 89:199–203). Several days after injury, MMP-2 expression is upregulated and latent enzyme is substantially converted to its active form (Ferguson et al. [2000] *Mol Cell Neurosci* 16:157–167).

In vitro degeneration results in a substantial increase in the neurite-promoting activity of nerve explants. This increase is blocked by the addition of MMP inhibitor, as is the coincidental increase in net gelatinolytic activity (demonstrated by in situ zymography). The rise in neurite-promoting activity occurs rapidly in the cultured nerve explants and in parallel with the upregulation and activation of MMP-2. In contrast, the initial effect of in vivo degeneration only suppresses the already low neurite-promoting activity of normal nerve, during which time there is no change in MMP-2 expression or activation in vivo. The neurite-promoting activity of transected nerve does, however, increase over time in vivo and this coincides with a burst of MMP-2 expression and activation (Ferguson and Muir, 2000, *Mol Cell Neurosci* 16:157–167; Shubayev and Myers, 2000, *Brain Res* 855:83–89).

In vitro assays indicate that nerve segments predegenerated in vivo have greater neurite-promoting activity than normal segments of nerve (Bedi et al. [1992] *Eur J Neurosci* 4:193–200; Agius et al. [1998] *J Neurosci* 18:328–338; Ferguson et al. [2000] *Mol Cell Neurosci* 16:157–167). However, in vivo studies testing predegenerated nerve grafts have produced conflicting results, especially when using cellular (live) nerve grafts (Gordon et al. [1979] *J Hand Surg [Am]* 4:42–47; Danielsen et al. [1994] *Brain Res* 666: 250–254; Hasan et al. [1996] *J Anat* 189(Pt 2):293–302). Nonetheless, predegeneration appears to be particularly advantageous for the enhancement of regeneration into acellular grafts (Ochi et al. [1994] *Exp Neurol* 128:216–225; Danielsen et al. [1995] *Brain Res* 681:105–108). This indicates that, in degeneration, cellular and molecular mechanisms act to enhance the growth-promoting properties of the basal lamina which then retains the ability to stimulate nerve regeneration after the cellular elements have been killed. In vitro predegeneration results in a substantial increase in the growth-promoting ability of acellular nerve grafts, that was readily demonstrated in the present invention's cryoculture and grafting models. Acellular nerve grafting is associated with a substantial latency in the onset of axonal regeneration (Danielsen et al. [1995] *Brain Res* 681:105–108).

Much of the research on nerve explant culture and nerve graft preservation has focused on the cold storage of nerve segments. Unlike the efforts to promote finite degeneration of nerve grafts in culture, cold storage methods aim to preserve the nerve in minimal and ischemic conditions that suppress cellular and proteolytic activities. Levi et al. (Levi A et al. [1994] *Glia* 10:121–131) found that cell viability decreases significantly after 1 week and only a few viable Schwann cells remained in nerve explants after 3 weeks of cold storage. Subsequently, Lassner et al. (Lassner et al. [1995] *J Reconstr Microsurg* 11:447–453) reported that culture medium (DMEM, rather than Cold Storage Solution) has a positive effect on maintaining Schwann cell viability and on the regenerative potential of nerve grafts stored in cold ischemic conditions. Although not beneficial for optimizing the growth-promoting potential of nerve grafts, continued cold storage does further decrease cell viability, immunogenicity and the concerns of immunorejection of allogenic nerve grafts (Evans et al. [1998] *Muscle Nerve* 21:1507–1522). For this reason, prolonged cold storage and freeze-killed nerve allografts result in better regeneration that fresh allografts (Evans et al. [1999] *Microsurgery* 19:115–127).

Accordingly, there remains a need in the art for a low risk adjunctive therapy to improve the outcome of conventional nerve repair.

BRIEF SUMMARY OF THE INVENTION

The subject invention concerns compositions and methods for promoting the repair of nerve tissue. In a preferred embodiment, the compositions of the subject invention comprise chondroitin sulfate proteoglycan (CSPG)-degrading enzymes. In one embodiment, a composition of the subject invention comprises a CSPG-degrading enzyme selected from the group consisting of chondroitinase, hyaluronidase, and matrix metalloproteinase (MMP), or combinations thereof. In a further embodiment, a composition of the subject invention comprises a CSPG-degrading enzyme selected from the group consisting of chondroitinase ABC, chondroitinase A, chondroitinase C, chondroitinase AC, hyaluronidase, MMP-2, and MMP-9, or combinations thereof.

The present invention also concerns methods to promote the repair of damaged nerve tissue in a human or animal. Methods of the present invention comprise administering one or more CSPG-degrading enzymes to a nerve repair, coaptation, graft, or damaged nerve tissue. The methods of the subject invention improve the ability of regenerating axons to traverse the nerve-nerve or nerve-graft interface and potentiates axonal growth within the basal lamina scaffold. The degradation of inhibitory CSPG creates a more permissive nerve substratum and allows axon sprouts greater access to Schwann cell basal lamina of the nerve, thereby increasing the number of axons that successfully penetrate damaged nerve tissue or implanted nerve grafts. The appropriate routing of the axon sprouts may also be enabled leading to further improvements in recovery of function.

The present invention also concerns methods of preparing nerve grafts by treatment with CSP-degrading enzymes. Preferably, the nerve graft (either allogenic or xenogenic) is fresh and not degenerated and is treated with CSPG-degrading enzymes either before or after the nerve graft is frozen. If treated while the cells of the graft are alive, the graft can be implanted as such or can then be freeze-killed to render it acellular. In one embodiment, the nerve tissue is rendered acellular after treatment. In a preferred embodiment, the nerve tissue is rendered acellular by freeze-killing.

The present invention also concerns methods of culturing fresh (or briefly preserved for transport) nerve tissue for subsequent implantation as a nerve graft into a human or animal. Preferably, the nerve tissue is harvested fresh from human or animal donor and cultured under physiological conditions that permit the tissue to degenerate and remodel ex vivo, promoting proliferation of Schwann cells within the tissue and activation of the basal lamina by endogenous processes. In one embodiment, the nerve tissue/graft is rendered acellular after culturing. In a preferred embodiment, the nerve tissue/graft is rendered acellular by freeze-killing.

The present invention further pertains to methods of providing nerve grafts for implantation into humans or animals. Preferably, the cross-sectional characteristics of the donor graft are similar to the cross-sectional characteristics of the nerve tissue at the implantation site.

BRIEF DESCRIPTION OF THE DRAWINGS

FIGS. 1A–1D show CSPG neoepitope immunofluorescence of chondroitinase-treated acellular nerve grafts. Acellular (freeze-killed) rat sciatic nerve segments were treated en bloc with chondroitinase ABC for 16 h in vitro. FIG. 1A shows neoepitope (chondroitinase-dependent) labeling with Ab1918, demonstrating that en bloc treatment with chondroitinase effectively permeated all nerve compartments and degraded CSPG side-chains. In FIG. 1B, the intensity of Ab1918 immunolabeling was not increased by additionally treating sections of the nerve shown in FIG. 1A with chondroitinase, indicating the initial en bloc treatment was thorough. In FIG. 1C, the structural integrity of Schwann cell basal laminae in chondroitinase-treated acellular nerve segments was shown by laminin immunofluorescence. FIG. 1D shows Ab1918 immunolabeling of chondroitinase-treated acellular interpositional nerve graft after 8 days in vivo.

In FIG. 8A, axons (small arrows) approach, traverse the distal coaptation, and grow diffusely within the host distal stump. In FIG. 8B, S-100 labeled Schwann cells are abundant in the distal host stumps, yet few if any invade the distal aspect of the grafts (which contains faint S-100 immunostaining associated with freeze-killed Schwann cell remnants).

FIG. 9A also demonstrates that, by virtue of the neoepitope labeling, CSPG side chains were effectively degraded in human nerve segments treated with chondroitinase.

As shown in FIG. 12C, similar results were obtained in crush-injured nerves which were examined 2 days after chondroitinase injection. The extent of CSPG degradation by in vivo injection of chondroitinase was examined by CSPG-neoepitope immunolabeling of nerves treated a second time with chondroitinase after the tissue was sectioned, as shown in FIG. 12D. The staining intensity observed in serial sections was not noticeably different after the second application (compare FIG. 12B and FIG. 12D), indicating the single in vivo injection of chondroitinase effectively degraded CSPG in the surrounding extracellular matrix.

FIGS. 13A and 13B show treatment with chondroitinase ABC did not alter axonal regeneration after nerve crush injury. Adult rats received bilateral sciatic nerve crush and one nerve was injected with chondroitinase ABC and the contralateral nerve received vehicle alone. Nerves were removed two days after injury and regenerating axons were labeled by GAP-43 immunocytochemistry. Regenerated axon profiles immediately distal to the nerve crush in two representative animals (each receiving vehicle and chondroitinase injections) are shown in FIG. 13A. As shown in FIG. 13B, GAP-43-immunolabeled axons were scored in serial sections of the distal nerves. There was no significant difference in axon regeneration in the chondroitinase-treated (Ch'ase) nerves compared to the vehicle-treated control nerves. Data represent the means (±SEM) of 6 chondroitinase-treated and 6 vehicle-treated nerves assessed at 0.56-mm intervals into the distal nerves.

FIGS. 14A and 14B show treatment with chondroitinase ABC markedly enhanced axon regeneration after nerve transection and neurorrhaphic repair. Adult rats received bilateral nerve transection and end-to-end repair. One nerve was injected with chondroitinase ABC and the contralateral nerve received vehicle alone. Nerves were removed four days after injury and regenerating axons were labeled by GAP-43 immunocytochemistry. Regenerated axon profiles immediately distal to the nerve coaptation in two representative animals (each receiving vehicle and chondroitinase injections) are shown in FIG. 14A. GAP-43-immunolabeled axons were scored in serial sections of the distal nerves as shown in FIG. 14B. Axon regeneration was significantly greater in the chondroitinase-treated (Ch'ase) nerves compared to the vehicle-treated controls. Data represent the means (±SEM) of 7 chondroitinase-treated and 7 vehicle-treated nerves assessed at 0.56-mm intervals into the distal nerves.

As shown in FIG. 15A, freshly excised rat sciatic nerve explants were cultured for 1, 2, 4, and 7 days in DMEM/N2 containing 0, 2, or 10% fetal bovine serum. As shown in FIG. 15B, nerve explants were cultured for 2 days in DMEM/N2 containing 2% serum (Culture Standard) without and with the addition of GM6001 (MMP inhibitor). The nerves were then cryosectioned and embryonic DRG neurons were seeded onto the tissue sections in DMEM/N2 containing NGF. After 24 hours, DRG neurons were immunostained for GAP-43 and neuritic growth was measured by digital photomicroscopy and image analysis. The control condition was normal nerve (0 days in culture). Data represent the mean neurite lengths (±SEM) of >250 neurons scored in each condition from at least 4 separate nerve explant cultures tested in 2 or more separate experiments.

As shown in FIGS. 17C and 17D, gelatinolytic activity was more intense and diffuse throughout the endoneurium in the cultured nerves. As shown in FIGS. 17E and 17F, gelatinolytic activity in nerves cultured in the presence of GM6001 was markedly decreased.

As shown in FIG. 18A, MMP-2 immunolabeling of culture nerves (2-day, 2% serum) was intense within Schwann cells and the surrounding basal laminae (inset). In FIG. 18B, S-100 immunolabeling showed the repositioning of an expanded population of Schwann cells within the nerve. As shown in FIG. 18C, MMP-9 immunolabeling was virtually absent within the nerve fascicles, except for a rare cellular profile. Some cells in the surrounding epineurium were labeled for MMP-9. In FIG. 18D OX42 labeling showed macrophages scattered throughout the epineurium and rarely within the nerve fascicles of cultured nerves.

In FIG. 19A, neurofilament immunolabeling showed the compact and contiguous formation of axons in normal nerve compared to the annular and fragmented axons found in cultured nerve explants (2-day, 2% serum) as shown in FIG. 19B (FIGS. 19A and 19B insets, longitudinal sections). As shown in FIG. 19C, immunolabeling for laminin indicated that basal laminae were structurally intact and that laminin expression was upregulated in Schwann cells (inset). As shown in FIG. 19D, the degeneration of axons and the extrusion of myelin by Schwann cells was especially evident in semi-thin sections stained with toluidine blue. Degenerative processes resulting in further myelin degeneration (collapse and condensation) and phagocytotic removal were not observed in the 2-d cultured nerve segments as shown in the inset of FIG. 19D.

In FIG. 20A, representative sections of control and predegenerated grafts from two animals are shown. Sections show the axonal regeneration at 1.5 mm into the grafts. Pixel values of the immunofluorescent images were inverted. As shown in FIG. 20B, quantitative analysis was performed at measured distances within the grafts. Data represent the means (±SEM) of 6 nerves in each condition.

DETAILED DISCLOSURE OF THE INVENTION

Figure 2:
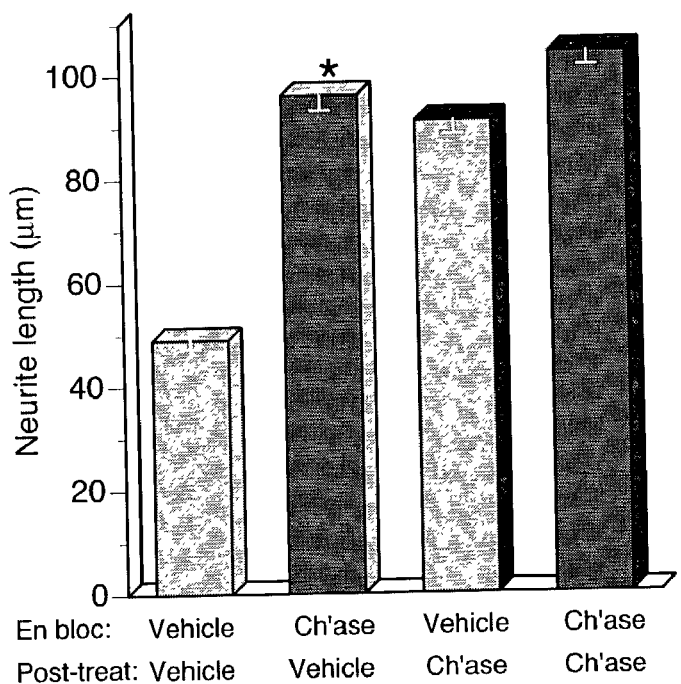
FIG. 2 shows inactivation of inhibitory CSPG by cryoculture bioassays of acellular nerve segments treated with chondroitinase. Acellular nerve segments were treated en bloc with chondroitinase ("Ch'ase") or vehicle alone. The nerves were sectioned and then treated additionally posttreated with chondroitinase or vehicle only. Dissociated chick embryonic DRG neurons were grown on the nerve sections for 24 h and neurite lengths were scored as described in Materials and Methods. Determinations were made by scoring at least 250 neurons in each condition. Results are expressed as means (–SEM) and statistical significance comparing the en bloc vehicle and chondroitinase conditions was determined using Student's t test. *P<0.001.

The subject invention provides compositions and methods for promoting the repair of nerve tissue. The compositions and methods of the subject invention can be employed to restore the continuity of nerve interrupted by disease, traumatic events or surgical procedures. The compositions and methods of the subject invention promote repair of nerve tissue by increasing the number of axons that successfully penetrate damaged nerve tissue or implanted nerve grafts, resulting in greater functional recovery.

In a preferred embodiment, the compositions of the subject invention comprise chondroitin sulfate proteoglycan (CSPG)-degrading enzymes. In one embodiment, a composition of the subject invention comprises a CSPG-degrading enzyme selected from the group consisting of chondroitinase, hyaluronidase, and matrix metalloproteinase (MMP), or combinations thereof. In a further embodiment, a composition of the subject invention comprises a CSPG-degrading enzyme selected from the group consisting of chondroitinase ABC, chondroitinase A, chondroitinase C, chondroitinase AC, hyaluronidase, MMP-2, and MMP-9, or combinations thereof.

The CSPG-degrading enzymes can be human, animal, or bacterial in origin, naturally occurring or recombinant. As used herein, the term "CSPG-degrading enzymes" is also intended to include biologically active fragments and variants of such enzymes, e.g., that retain a substantial amount of their CSPG-degradative activity. The compositions of the subject invention can include an appropriate pharmaceutical carrier. The subject invention further concerns nerve tissue treated with one or more CSPG-degrading enzymes.

In addition to one or more CSPG-degrading enzymes, the compositions of the subject invention can further comprise biologically or pharmacologically active molecules, such as growth factors. Such growth factors include, but are not limited to, nerve growth factor (NGF), fibroblast growth factors (FGF-1 and 2), epidermal growth factor (EGF), ciliary neurotrophic factor (CNTF), brain derived neurotrophic factor (BDNF), neurotrophin-3, -4, and -5 (NT-3, -4, and -5), insulin-like growth factor-I and -II (IGF-I, II), transforming growth factor (TGF), glial growth factor-2 (GGF-2), vascular endothelial growth factor (VEGF), granulocyte-macrophage colony stimulating factor (GM-CSF), and lymphocyte infiltrating factor/cholinergic differentiating factor (LIF/CDF). Such molecules can be obtained naturally or by recombinant DNA techniques. Fragments or variants of such molecules that retain their biological or pharmacological activities can also be used.

The present invention also concerns methods to promote the repair of damaged nerve tissue in a human or animal. Methods of the present invention comprise administering one or more CSPG-degrading enzymes to a nerve graft or damaged nerve tissue. The methods of the subject invention improve the ability of regenerating axons to traverse the nerve-nerve and nerve-graft interface and potentiates axonal growth within its basal lamina scaffold. The degradation of inhibitory CSPG creates a more permissive nerve substratum and allows axon sprouts greater access to Schwann cell basal lamina of the nerve, thereby increasing the number of axons that successfully penetrate damaged nerve tissue or implanted nerve grafts.

Application of CSPG-Degrading Enzymes to Damaged Nerve. In one embodiment, the CSPG-degrading enzymes are applied to damaged nerve, the site of nerve damage or the site of nerve damage repair. In a preferred embodiment, the CSPG-degrading enzymes are applied to the site of primary nerve repair involving coaptation of severed or trimmed nerve (i.e., end-to-end nerve coaptation). The damage to the nerve can represent a nerve transection (neurotmesis), wherein the nerve is partially or fully severed or a small region damaged and surgically removed, and epineurial coaptation (neurorrhaphy) is the primary method of repairing the damaged nerve. For example, the compositions and methods of the subject invention can be used to promote repair of nerve damage that involves a disruption in the continuity of at least one of the nerve sheaths of the damaged nerve, such as the basal lamina, perineurium, or epineurium. Preferably, the surgical repair attempts to realign nerve elements.

In a specific embodiment, the damage to the nerve represents a nerve crush injury (axonotmesis) or more extreme damage, where there is axotomy but the continuity of the sheath remains intact or is somewhat compromised. In the case of axonotmesis, axons typically regenerate without surgical intervention.

In some cases, a segment of the nerve is diseased, irreparably damaged or obliterated and is surgically removed. Repair may involve implantation of a graft or prosthesis to bridge the gap. The implant may be natural (e.g., nerve or vascular graft), a natural derivative (e.g., biopolymer tube) or synthetic conduit (silicone tube). These are connected to the cut nerve ends. In a specific embodiment, the CSPG-degrading enzymes are applied at the connection sites, at either or both ends. For example, the CSPG-degrading enzymes can be applied to one or both points of host-graft interface on an interpositional graft. The CSPG-degrading enzymes can be applied before, during, or after surgical repair of the damaged nerve tissue or implantation of the graft within the recipient.

Application of CSPG-Degrading Enzymes to Nerve Grafts. In one embodiment, the CSPG-degrading enzymes are applied to a nerve graft. When the CSPG-degrading enzymes are applied to a nerve graft, the entire graft can be treated. The CSPG-degrading enzymes can be applied to the entire nerve graft, en bloc. This application is a pretreatment or incubation prior to implantation and may or may not involve procedures to remove the applied enzyme. The en bloc treatment can be applied to living (fresh) or previously frozen nerve grafts. The en bloc treatment does not preclude, but may be used in conjunction with, additional application of CSPG-degrading enzymes at the site of coaptation with host nerve.

According to the methods of the subject invention, the CSPG-degrading enzyme can be applied to the nerve graft or damaged nerve tissue, or both. The CSPG-degrading enzyme can be applied to a nerve graft before, during, or after implantation. The CSPG-degrading enzyme can be applied to any portion of the graft, such as the end or ends to be joined to the stump of the damaged nerve. If the CSPG-degrading enzyme is applied to the damaged nerve, the enzyme can be applied to any area of the damaged nerve that promotes repair of the damaged nerve, such as at the site of damage or adjacent to the site of damage. The CSPG-degrading enzymes can be placed in a culture medium for application to the nerve graft. The culture medium can be undefined medium, defined medium, or defined medium supplemented with serum for example. The subject invention also includes storage solutions for storage of nerve grafts prior to implantation. The storage solution contains a culture medium, as indicated above, and at least one CSPG-degrading enzyme. The storage solution can also include a tissue adhesive, such as fibrin glue. The storage solution can also include other biologically active agents, such as the growth factors listed above.

As used herein, the term "graft" refers to any tissue intended for implantation within a human or animal. Various types of graft are encompassed within the subject invention, such as autografts, syngrafts, allografts, and xenografts. The size (e.g., length and diameter) of the graft is not critical to the subject invention. For example, the length of the nerve graft can be from about 1 centimeter to about 10 centimeters, or over about 10 centimeters. The diameter of the nerve graft can match that of any injured nerve or part of a nerve, as needed. The nerve graft can be a structurally complete segment of nerve to bridge a gap along the length of the recipient's nerve or to replace the distal end, i.e., for end-to-end grafting. Alternatively, the nerve graft can be a partial nerve segment, or eccentrically-shaped (e.g., a nerve flap), and intended to reconstruct a lacerated nerve that has some structural disruption, but retains its physical continuity.

Optionally, the CSPG-degrading enzyme can be applied to the injured nerve or nerve graft in conjunction with a tissue adhesive, such as a biological glue. Preferably, the biological glue is a fibrin-containing adhesive, such as fibrin glue, fibrin sealant, or platelet gel. Biological glues are well known in the surgical art (Suri A et al. [2002] *Neurol. India* 50:23–26; Alibai E et al. [1999] *Irn J. Med. Sci.* 24(3&4): 92–97; Sames M et al. [1997] Physiol. Res. 46(4):303–306; Jackson M et al. [1996] *Blood Coag. Fibrinolysis* 7:737–746; Fasol R et al. [1994] *J. Thorac. Cardiovasc. Surg.* 107:1432–1439). As used herein, the terms "fibrin glue", "fibrin sealant", and "fibrin tissue adhesive" are used interchangeably to refer to a group of formulations containing fibrinogen and thrombin, which lead to the formation of a fibrin clot at the site of application. The tissue adhesive can be applied simultaneously or consecutively with the CSPG-degrading enzyme. The tissue adhesive can be applied to the injured nerve and/or nerve graft within the same formulation as the CSPG-degrading enzyme, or in a separate formulation. Preferably, the adhesive will not contain substances such as laminin that will attract the growth of axons from the remaining nerve structure or contain substrates or inhibitors for the applied enzyme(s) that will compete with or inhibit activity of the enzyme(s).

The CSPG-degrading enzymes used in the subject invention can be applied to the nerve graft or damaged nerve tissue by various means and in a variety of formulations. As used herein, the terms "applied", "administered", "contacted", and "treated" are used interchangeably. For example, the CSPG-degrading enzymes can be applied to the nerve graft or damaged nerve tissue topically (e.g., drop-wise), or administered by injection. Topical application or local administration by injection are preferred for greater control. Further, the CSPG-degrading enzymes, or compositions containing such enzymes, are preferably applied as a liquid, flowable, formulation. The CSPG-degrading enzyme or enzymes can also be adsorbed onto a porous substance, or formulated into an ointment, salve, gel, cream, or foam, for example.

The subject invention also includes kits for promoting repair of damaged nerve tissue. The kits of the invention include a first compartment containing at least one CSPG-degrading enzyme and a second compartment containing a tissue adhesive, such as those described herein. Optionally, the kits can include a third compartment for mixing the CSPG-degrading enzyme or enzymes and the tissue adhesive. The kits can be used for repair of damaged nerve tissue directly, or indirectly, via nerve graft. The kit can include packaging of various materials known in the art, such as plastic, glass, and/or paper products.

Pharmaceutical Compositions. One or more CSPG-degrading enzymes can be incorporated into a pharmaceutical composition suitable for administration to a patient, e.g., a human or animal. Such compositions typically comprise at least one CSPG-degrading enzyme and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Supplementary active compounds can also be incorporated into the compositions. Preferably, the pharmaceutical compositions include at least one CSPG-degrading enzyme and a tissue adhesive, such as fibrin glue.

The pharmaceutical compositions of the subject invention can be formulated according to known methods for preparing pharmaceutically useful compositions. Formulations are described in a number of sources which are well known and readily available to those skilled in the art. For example, Remington's Pharmaceutical Science (Martin E W [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules, vials, and disposable syringes made of glass or plastic, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that, in addition to the ingredients particularly mentioned above, the formulations of the subject invention can include other agents conventional in the art having regard to the type of formulation in question. The pharmaceutical compositions can be included in a container, pack, or dispenser, together with instructions for administration.

The CSPG-degrading enzymes can be formulated in a carrier appropriate for the mode of administration, e.g., saline or aqueous buffer. The CSPG-degrading enzymes can also be contained within, or associated with, a controlled release formulation. Such materials include, but are not limited to, biodegradable matrices and particles, such as liposomes, lipospheres, or vesicles. The controlled release formulation can be a biodegradable polymeric matrices. The CSPG-degrading enzymes can also be applied as a gel or film, or contained within a synthetic graft or implant.

The CSPG-degrading enzymes can be prepared with carriers that will protect the enzymes against rapid elimination from the body, such as a controlled release formulation, including implants and microencapsulated delivery systems. Preferably, the carrier is biodegradable and/or bioresorbable. Biodegradable, biocompatible polymers can be utilized in the controlled release formulation, such as ethylene vinyl acetate, polyanhydrides, polyglycolic acid, collagen, polyorthoesters, and polylactic acid.

The controlled release formulation can be particulate in nature (e.g., of micro- or nano-size scale), such as a sphere or capsule. The particle can have a core containing one or more CSPG-degrading enzymes, which is encapsulated by an outer layer or shell. The outer shell can be degradable by the encapsulated CSPG-degrading enzyme (such that the shell is degraded from within). For example, the shell can be at least partially composed of hyaluronan, such that when the hyaluronan within the shell is degraded (partially or completely) by the encapsulated CSPG-degrading enzyme or enzymes, the CSPG-degrading enzyme or enzymes are released. Alternatively, the shell can be degraded by another degrading agent that is either exogenously applied or that is present within the in vivo environment (such that the shell is degraded from without).

U.S. Pat. No. 5,320,837 describes controlled release preparations obtained by reacting an enzyme having an amino group, such as hyaluronidase or chondroitinase, with a copolymer of maleic anhydride and a copolymerizable polyalkylene glycol ether. The reaction product is soluble in water and/or organic solvent and capable of slowly releasing the enzyme upon hydrolysis.

U.S. Pat. No. 4,933,185 describes a controlled release system for delivery of a biologically active substance consisting of an enzyme (such as hyaluronidase) encapsulated within a microcapsule having a core formed of a polymer, such as an ionically cross-linked polysaccharide, which is specifically degraded by the enzyme and a rate controlling skin. The integrity of the skin is lost when the core is degraded, causing a sudden release of the biologically active substance from the capsule. The controlled release system in the '185 patent can be utilized to deliver a CSPG-degrading enzyme or enzymes. For example, the CSPG-degrading enzyme or enzymes can function as the biologically active substance, or the core degrading enzyme, or both.

The controlled release formulation can provide an initial exposure of the CSPG-degrading enzyme or enzymes, followed by one or more delayed exposures following a specific period of time. Alternatively, the controlled release formulation can cause a single delayed release of the CSPG-degrading enzyme or enzymes. Alternatively, the continuous release formulation can allow for continuous release of the CSPG-degrading enzyme or enzymes. Optionally, the continuous release of the CSPG-degrading enzyme or enzymes can be in conjunction with one or more pulsed releases.

The carrier of the CSPG-degrading enzymes, such as an implant, can be of a size and shape appropriate for the particular application. Thus, the carrier can be of a desired volume and in a desired shape, designed in due consideration of the region of the living body at which the carrier is put to use. Examples of shapes include, but are not limited to, a cylinder, a semicylinder, or a ring. The carrier can be a pad, a wrap, a sheet, a bar, or a thread that is contacted with the injured nerve or nerve graft. Preferably, the carrier does not have shape edges or corners that may irritate or otherwise stimulate the surrounding tissue of the living body.

The amount of CSPG-degrading enzyme or enzymes released from the carrier and the duration of release can be controlled within appropriate ranges. The carrier can be fixed or secured to the graft or injured nerve or to tissue adjacent to the graft or injured nerve. The carrier can continuously release the CSPG-degrading enzyme or enzymes at the nerve injury site over a period of time, such as, for example, 24 hours to three months.

Depending upon the particular carrier utilized, the CSPG-degrading enzyme or enzymes can be contained within, coated, or otherwise associated with the carrier during or after its manufacture. For example, the CSPG-degrading enzyme or enzymes can be associated with a commercial product.

The carrier can also function to deliver other biologically active agents, such as cells (e.g., Schwann cells) or growth factors, with the CSPG-degrading enzymes. The cells delivered by the carrier can be derived from the patient, or from another source of the same species or a different species. The cells delivered by the carrier can be genetically modified to produce a biologically active agent.

In one embodiment, the carrier is a surgical cuff, such as those described in U.S. Pat. Nos. 4,602,624, 5,487,756, and published U.S. patent application No. 2002/0071828, which can be implanted closely adjacent to the nerve graft or injured nerve (e.g., at the site of damage). The cuff of the subject invention includes a sleeve to be applied to the nerve graft or damaged nerve tissue. The sleeve can be a variety of shapes. For example, the sleeve can be a tubular prosthesis or wrap that at least partially or fully encircles the damaged nerve and/or nerve graft and may include any device that is compatible with the intended use of joining the ends of an injured nerve either directly or indirectly through a nerve graft, using a cuffing technique, to restore nerve continuity. If the cuff is tubular in shape, the cuff can optionally include a longitudinal slit with abutting first and second edges for ease of application to a nerve graft or damaged nerve. For example, the first and second abutting edges of the longitudinal slit can be in separable contact with one another, permitting the separation of the abutting edges of the slit, exposing the lumen of the tubular sleeve. The damaged nerve and/or nerve graft can then be inserted into the lumen, allowing the abutting edges of the longitudinal slit to return to being in separable contact with one another holding the damaged nerve and/or nerve graft together and available for exposure to CSPG-degrading enzymes.

Optionally, the surgical cuff can be secured to the nerve using conventional suture techniques or a tissue adhesive, such as a biological glue that can be applied to the nervous system, or other means. Preferably, the biological glue is a glue containing fibrin, such as BIOCOLLE (BIOTRANSFUSION), CRTS, (Lille), ISSUCOL (IMMUNO AG, Vienna Austria), and the like. The cuff can be a rigid support or, for example, a self-curling sheet. The self-curling sheet can automatically encircle the damaged nerve an/or nerve graft when contacted to the respective tissue. The cuff can be permeable, impermeable, or semi-permeable. Optionally, the cuff can include a means for electrically stimulating the nerve graft or damaged nerve and/or a means for recording nerve electrical activity within the nerve graft or damaged nerve, such as that described in U.S. Pat. No. 5,487,756. Preferably, the CSPG-degrading enzyme or enzymes are released or otherwise operate from the inner surface of the cuff, i.e., that surface facing the nerve graft or damaged nerve.

The surgical cuff can provide the CSPG-degrading enzyme or enzymes to the nerve graft or damaged nerve via a delivery system, such as a reservoir or an expression system, such as the adenovirus constructs described in published U.S. patent application No. 2002/0071828. Expression systems for chondroitin lyase enzymes are known in the art, some of which are described in U.S. Pat. Nos. 6,054,569; 6,093,563; published U.S. patent application No. 2001/0034043; and Tralec, A. L. [2000] *Appl. Environ. Microbiol.* 66:29–35.

The surgical cuff can be composed of a variety of synthetic material(s), such as silicone, PAN/PVC, PVFD, polytetrafluoroethylene (PTFE) fibers or acrylic copolymers. In a specific embodiment of the invention, the use of a cuff consisting of or based on biomaterials, such as in particular cross-linked collagen, bone powder, carbohydrate-based polymers, polyglycolic/polylactic acid derivatives, hyaluronic acid esters, or chalk-based supports, is preferred. Preferably, collagen or silicone is used within the framework of the present invention. It may be collagen of, for example, human, bovine or murine origin. More preferably, a cuff consisting of a bilayer of type I or III or IV, advantageously IV/IVox, collagen, or of silicone, is used. There may be mentioned, by way of a specific example, a SILASTIC cuff (DOW-CORNING), consisting of silicone. Moreover, the cuff may have advantageously a tubular shape, of cylindrical or angular section. The diameter of the cuff can be adjusted by persons skilled in the art according to the desired applications. In particular, for stimulating the regeneration of a peripheral nerve, a relatively small diameter, from 0.05 to 15 mm, can be used. More preferably, the inner diameter of the cuff is between 0.5 and 10 mm. For spinal cord regeneration applications, cuffs with a larger inner diameter can be chosen. In particular, for these applications, the cuffs used have an inner diameter which may be as high as 15 to 20 mm, depending on the relevant nerve section. For bridging a root avulsed at the level of the brachial plexus, the diameter of the cuff advantageously corresponds to the diameter of the root. The length of the cuff is generally determined by the size of the loss of substance to be compensated for. Cuffs with a length of between 0.5 and 5 cm can be used. Preferably, the length of the cuff remains less than 5 cm, losses of substance greater than 5 cm being less frequent.

The CSPG-degrading enzymes can be applied to the nerve graft or damaged nerve tissue in various concentrations, but are preferably applied in a concentrated form. Ideal concentrations will vary with nerve size and enzyme. For example, chondroitinase can be applied in a concentration ranging from about 10 units/mL to about 1000 units/mL. Preferably, the chondroitinase is applied to the nerve graft or damaged nerve tissue at a concentration range from about 100 units/mL to about 500 units/mL. MMPs can be applied in a concentration ranging from about 0.1 $\mu$g/mL to about 100 $\mu$g/mL. Preferably, the MMP is applied in a concentration ranging from about 10 $\mu$g/mL to about 50 $\mu$g/mL.

As indicated above, according to the methods of the subject invention, the CSPG-degrading enzyme or enzymes can be administered to a nerve graft or injured nerve tissue in conjunction with a biologically active molecule, such as a growth factor. Other biologically active agents that can be administered with the CSPG-degrading enzyme or enzyme include genetically-modified or non-genetically modified cells. Thus, the compositions of the subject invention can include such cells. The cells can be non-stem cells (mature and/or specialized cells, or their precursors or progenitors) or stem cells. Thus, the administered cells can range in plasticity from totipotent or pluripotent stem cells (e.g., adult or embryonic), precursor or progenitor cells, to highly specialized or mature cells, such as those of the central or peripheral nervous system (e.g., Schwann cells).

Stem cells can be obtained from a variety of sources, including fetal tissue, adult tissue, cord cell blood, peripheral blood, bone marrow, and brain, for example. Stem cells and non-stem cells (e.g., specialized or mature cells, and precursor or progenitor cells) can be differentiated and/or genetically modified. Methods and markers commonly used to identify stem cells and to characterize differentiated cell types are described in the scientific literature (e.g., Stem Cells: Scientific Progress and Future Research Directions, Appendix E1–E5, report prepared by the National Institutes of Health, June, 2001). The list of adult tissues reported to contain stem cells is growing and includes bone marrow, peripheral blood, brain, spinal cord, dental pulp, blood vessels, skeletal muscle, epithelia of the skin and digestive system, cornea, retina, liver, and pancreas.

According to the methods of the subject invention, genetically modified hosts, such as recombinant cells, can be administered to the nerve graft or damaged nerve tissue. The hosts can be genetically modified to produce one or more CSPG-degrading enzymes. Preferably, the CSPG-degrading enzyme is secreted from the recombinant cell. For example, expression systems for chondroitin lyase enzymes are known in the art, some of which are described in U.S. Pat. Nos. 6,054,569; 6,093,563; published U.S. patent application No. 2001/0034043; and Tralec, A. L. [2000] *Appl. Environ. Microbiol.* 66:29–35. Optionally, the recombinant host is genetically modified to recombinantly produce other biologically active agents, in addition to the CSPG-degrading enzyme.

Nucleic acid molecules encoding one or more CSPG-degrading enzymes can be inserted into vectors and used as gene therapy vectors. Gene therapy vectors can be delivered to a patient by, for example, intravenous injection, local administration, or by stereotactic injection. The pharmaceutical preparation of the gene therapy vector can include the gene therapy vector in an acceptable diluent, or can comprise a slow release carrier in which the gene delivery vehicle is imbedded or otherwise associated. In addition, the pharmaceutical preparation can include a therapeutically effective amount of cells which recombinantly produce the CSPG-degrading enzyme.

The various methods employed in the genetic modification of host cells are well known in the art and are described, for example, in Sambrook et al. (1989) *Molecular Cloning: A Laboratory Manual,* second edition, volumes 1–3, Cold Spring Harbor Laboratory, New York, and Gloves, D. M. (1985) *DNA Cloning, Vol. I: A Practical Approach,* IRL Press, Oxford. Thus, it is within the skill of those in the genetic engineering art to extract DNA from its source, perform restriction enzyme digestions, electrophorese DNA fragments, tail and anneal plasmid and insert DNA, ligate DNA, transform cells, e.g., prokaryotic and eukaryotic cells, prepare plasmid DNA, electrophorese proteins, and sequence DNA.

To reduce immunogenicity, nerve grafts used in the subject invention can be made acellular by a variety of methods known to those of ordinary skill in the art. For example, the nerve tissue can be made acellular by freeze-killing, as described in the Materials and Methods section, or by chemical extraction with detergents (Sondell M et al. [1998] *Brain Res* 795:44–54). The nerve grafts can be rendered acellular before, during, or after application of one or more CSPG-degrading enzymes.

In Vitro Nerve Culture. The present invention also concerns methods of culturing nerve tissue for implantation into a human or animal. The culture methods of the subject invention involve "predegenerating" the nerve tissue in vitro, which, following engraftment, improves the ability of regenerating axons to traverse the interface between the graft and host nerve tissue. Without being bound by theory, the culturing methods of the subject invention allow the living nerve cells to express CSPG-degrading enzymes and promote Schwann cell proliferation, as would occur naturally in vivo during the remodeling process of nerve degeneration.

The method of in vitro culture involves culturing the nerve tissue under conditions that permit the nerve tissue to grow in vitro and increase the neurite-promoting activity of the nerve tissue when subsequently implanted as a graft. The increase in neurite-promoting activity can be as determined by an in vitro neurite outgrowth assay of the nerve tissue, such as the cryoculture bioassay described herein.

Alternatively, an in vivo neurite outgrowth assay of the nerve tissue could also be utilized. Methods for assaying neurite outgrowth are known in the art and typically involve qualitatively or quantitatively determining the extent of neurite outgrowth on a solid support, such as a microplate or microscope slide. Standard fluorescence an be utilized.

The methods of the subject invention can comprise isolating nerve tissue from a human or animal and culturing the nerve tissue for a short period of time in vitro, ranging from about 24 hours to about 96 hours. Longer incubations in vitro can result in deterioration and loss of growth-promoting properties. Preferably, the nerve tissue is cultured from about 24 hours to about 72 hours. More preferably, the nerve tissue is cultured for about 48 hours.

The nerve tissue can be cultured at a temperature within a range of about 10° C. to about 37° C. Preferably, the nerve tissue is cultured within a range of about 30° C. to about 37° C. More preferably, the nerve tissue is cultured at about 37° C.

The nerve tissue can be cultured in defined medium or medium supplemented with serum. The defined medium can be, for example, N2 medium or Dulbecco's Modified Eagle Medium (DMEM). If medium supplemented with serum is used, the serum can be human or animal, such as fetal bovine serum. Preferably, the nerve tissue is cultured in defined medium. In one embodiment, the nerve tissue is a nerve graft that is rendered acellular after culturing and prior to implantation within a host. In a preferred embodiment, the nerve graft is rendered acellular by freeze-killing. While no exogenous enzymes are necessary to carry out the culture methods of the subject invention, the methods can further comprise contacting the nerve tissue with one or more CSPG-degrading enzymes.

The present invention further pertains to methods of providing nerve grafts for implantation into humans or animals. Preferably, the cross-sectional characteristics of the nerve graft are similar to the cross-sectional characteristics of the host nerve tissue at the implantation site, e.g., the host's proximal and distal nerve stump. In one embodiment, the method of the subject invention comprises generating digital image data of the nerve stump cross section within a potential host (i.e., graft recipient), analyzing the image data to define coordinate locations of nerve elements and their diameter to produce a recipient template, and comparing the recipient template data to donor template data that can be stored in memory. The donor template data represents the digital image data from a "bank" of stored nerve grafts. The stored nerve graft with the highest degree of structural element alignment with the recipient's nerve stump can then be selected for implantation within the recipient. The relevant parameters include the diameter, thickness, and/or spatial arrangement (i.e., boundaries) of one or more of the structural elements, which include, but are not limited to, epineurium, fascicular groups, fascicles, myelin sheath, and axons. Therefore, alignment between the nerve graft and the host nerve can be maximized. Preferably, the nerve graft selected is one with a similar cross-sectional arrangement of fascicular groups and axons.

U.S. Pat. No. 5,231,580 describes a variety of methods for determining the characteristics of nerve. The generation of the digital image data can be achieved using methods and devices well known in the art, such as a digital camera. Analysis of the image data and comparison of the recipient template data to the stored donor template data can be achieved, for example, through an algorithm capable of image scanning, analysis, and pattern recognition. To select the closest match between nerve graft and recipient nerve, threshold values of similarity can be established.

The methods and compositions of the subject invention are applicable to nerve tissue of both the central nervous system (CNS) and peripheral nervous system (PNS). For example, nerve grafts of the subject invention can be used as interpositional nerve grafts in the PNS or as bridges in the brain and spinal cord and any extensions thereof.

The CSPG-degrading enzymes used in the subject invention can be obtained from a variety of sources, including organisms that produce the enzyme naturally or organisms that produce (or overproduce) the enzyme through genetic modification (producing a recombinant enzyme). For example, the CSPG-degrading enzymes can be obtained from bacterial sources, including those that naturally produce the enzyme, or those that have been genetically modified to produce (or overproduce) the enzyme. CSPG-degrading enzymes can also be obtained from mammalian sources, including those mammals that naturally produce the enzyme or those mammals that have been genetically modified to produce (or overproduce) the enzyme. Alternatively, the CSPG-degrading enzyme can be chemically synthesized.

As used herein, the "proximal" part is intended to mean the part of the axon that remains in continuity with the neuron cell bodies or the part of the nerve containing these axons. The "distal" part is intended to mean the part of the axon that becomes disconnected from the neuron cell body or the part of the nerve containing these disconnected axons.

In the case of a peripheral nerve lesion, its proximal part is that which is connected to the ganglia or spinal cord. The distal part of the peripheral nerve is intended to mean the peripheral-most part of the nerve that is connected to the motor endplate (neuromuscular junction) or sensory organs. In the case of a lesion of the spinal cord, the proximal part is that which is in contact with nuclei or more anterior. The distal part is intended to mean that part which extends to a terminal synapse.

The terms "treating" or "treatment", as used herein, refer to reduction or alleviation of at least one adverse effect or symptom associated with the particular nerve damage suffered by the patient.

As used herein, the term "stem cell" is an unspecialized cell that is capable of replicating or self renewal, and developing into specialized cells of a variety of cell types. The product of a stem cell undergoing division is at least one additional stem cell that has the same capabilities of the originating cell. For example, under appropriate conditions, a hematopoietic stem cell can produce a second generation stem cell and a neuron. Stem cells include embryonic stem cells (e.g., those stem cells originating from the inner cells mass of the blastocyst) and adult stem cells (which can be found throughout the more mature animal, including humans). As used herein, stem cells are intended to include those stem cells found in animals that have matured beyond the embryonic stage (e.g., fetus, infant, adolescent, juvenile, adult, etc.).

As used herein, the term "progenitor cell" (also known as a "precursor cell") is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the term "co-administration" and variations thereof refers to the administration of two or more agents simultaneously (in one or more preparations), or consecutively.

As used herein, the term "combination" includes subcombinations. For example, a combination of the CSPG-degrading enzymes chondroitinase ABC, chondroitinase A, chondroitinase C, chondroitinase AC, hyaluronidase, MMP-2, and MMP-9, would include subcombinations of chondroitinase ABC and MMP-2, for example.

As used herein, the term "biological activity" or "biologically active" is intended to refer to the activity associated with the particular agent, molecule, compound, etc. For example, the biological activity exhibited by CSPG-degrading chondroitinases is degradation of CSPG. Preferably, the CSPG-degrading activity includes cleavage or lysis of chondroitin-4-sulfate, chondroitin-6-sulfate, or both chondroitin-4-sulfate and chondroitin-6-sulfate. Hence, biologically active fragments and variants of specific CSPG-degrading enzymes exhibit CSPG-degrading activity, as well. Likewise, biologically active fragments of growth factors, such as fibroblast growth factor-1, exhibit the biological activity normally associated with that growth factor.

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides. The term "genetic modification" is not intended to include naturally occurring alterations such as that which occurs through natural viral activity, natural genetic recombination, or the like.

Various vectors can be utilized to carry out genetic modification according to the subject invention. The vectors can be vaccine, replication, or amplification vectors. In some embodiments of this aspect of the invention, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations of the aforementioned vector sources, such as those derived from plasmid and bacteriophage genetic elements (e.g., cosmids and phagemids).

As indicated above, vectors utilized to carry out genetic modification can also comprise elements necessary to provide for the expression and/or the secretion of a polypeptide, such as a CSPG-degrading enzyme, or a biologically active fragment or variant thereof, encoded by the nucleotide sequences of the invention in a given host cell. The vector can contain one or more elements selected from the group consisting of a promoter, signals for initiation of translation, signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, the vector comprises a promoter operably linked to a protein or peptide-encoding nucleic acid sequence, one or more origins of replication, and, optionally, one or more selectable markers (e.g., an antibiotic resistance gene). Non-limiting exemplary vectors for the expression of the polypeptides of the invention include pBr-type vectors, pET-type plasmid vectors (PROMEGA), pBAD plasmid vectors (INVITROGEN) or those provided in the examples below. Furthermore, vectors according to the invention are useful for transforming host cells for the cloning or expression of the nucleotide sequences of the invention.

Promoters which may be used to control expression include, but are not limited to, the CMV promoter, the SV40 early promoter region (Bemoist and Chambon [1981] *Nature* 290:304–310), the promoter contained in the 3' long terminal repeat of Rous sarcoma virus (Yamamoto et al. [1980] *Cell* 22:787–797), the herpes thymidine kinase promoter (Wagner et al. [1981] *Proc. Natl. Acad. Sci. USA* 78:1441–1445), the regulatory sequences of the metallothionein gene (Brinster et al. [1982] *Nature* 296:39–42); prokaryotic vectors containing promoters such as the β-lactamase promoter (Villa-Kamaroff et al. [1978] *Proc. Natl. Acad. Sci. USA* 75:3727–3731), or the tac promoter (DeBoer et al. [1983] *Proc. Natl. Acad. Sci. USA* 80:21–25); see also, "Useful Proteins from Recombinant Bacteria" in *Scientific American*, 1980, 242:74–94; plant expression vectors comprising the nopaline synthetase promoter region (Herrera-Estrella et al. [1983] *Nature* 303:209–213) or the cauliflower mosaic virus 35S RNA promoter (Gardner et al. [1981] *Nucl. Acids Res.* 9:2871), and the promoter of the photosynthetic enzyme ribulose biphosphate carboxylase (Herrera-Estrella et al. [1984] *Nature* 310:115–120); promoter elements from yeast or fungi such as the Gal 4 promoter, the ADC (alcohol dehydrogenase) promoter, PGK (phosphoglycerol kinase) promoter, and/or the alkaline phosphatase promoter.

The subject invention also provides for the use of "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological or serological activity as the native (naturally occurring) CSPG-degrading enzyme. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences used in the present invention can have 20, 21, 22, 23, 24,25,26,27,28,29,30,31,32,33,34,35,36,37,38,39,40,41, 42,43,44,45,46,47,48, 49,50,51,52,53,54,55,56,57,58,59,60, 61,62,63,64,65,66,67,68,69,70,71,72,73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequence encoding the CSPG-degrading enzyme.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85(8):2444–2448; Altschul et al. [1990] *J. Mol. Biol.* 215 (3):403–410; Thompson [1994] *Nucleic Acids Res.* 22(2): 4673–4680; Higgins et al. [1996] *Methods Enzymol.* 266: 383–402; Altschul et al. [1990] *J. Mol. Biol.* 215(3):403–410; Altschul et al. [ 1993] *Nature Genetics* 3:266–272).

Cells or tissue administered to a patient according to the methods of the subject invention can be derived from humans or other mammals, including non-human primates, rodents, and porcines, for example. Specific examples of source species include, but are not limited to, humans, non-human primates (e.g., apes, chimpanzees, orangutans, monkeys); domesticated animals (pets) such as dogs, cats, guinea pigs, hamsters, Vietnamese pot-bellied pigs, rabbits, and ferrets; domesticated farm animals such as bovines, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, elephant seals, porpoises, dolphins, and whales.

Likewise, mammalian species which benefit from the disclosed methods of treatment include, and are not limited to, humans, non-human primates (e.g., apes, chimpanzees, orangutans, monkeys); domesticated animals (e.g., pets) such as dogs, cats, guinea pigs, hamsters, Vietnamese pot-bellied pigs, rabbits, and ferrets; domesticated farm animals such as bovines, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales.

All patents, patent applications, provisional patent applications, and publications referred to or cited herein are incorporated by reference in their entirety, as are co-filed U.S. patent application Ser. No. 10/218,316, "Materials and Methods for Nerve Repair"; and U.S. patent application Ser. No. 10/218,315, "Materials and Methods for Nerve Grafting", including all figures, tables, drawings, nucleotide sequences, and amino acid sequences, to the extent they are not inconsistent with the explicit teachings of this specification.

MATERIALS AND METHODS

Surgical procedures for nerve transection and nerve crush experiments. All surgical procedures were performed according to Institutional Animal Care and Use Committee (IACUC) approved protocols. Young adult SPRAGUE DAWLEY rats (HARLAN Indianapolis, Ind.) were deeply anesthetized with xylazine (15 mg/kg, i.m.) followed by ketamine-HCl (110 mg/kg, i.p.). Six animals received bilateral nerve crush injuries. Sciatic nerves were exposed and then crushed with firm pressure for thirty seconds with a DUMONT #5 forceps at a site 4 mm distal to the tendon of the internal obdurator. The crush site was marked with an epineurial suture. In a separate set of experiments, eight rats received bilateral sciatic nerve transection injuries using serrated scissors. The proximal and distal stumps were coated by epineurial neurorrhaphy using 9–0 ETHILON sutures. Fibrin glue (fibrinogen and thrombin) was then applied to stabilize the union. In both injury models, the right sciatic nerves were injected 2-mm distal to the injury with chondroitinase ABC (1 U in 2 $\mu$l) (high-purity, protease-free; SIGMA CHEMICAL CO., St. Louis, Miss.). Left sciatic nerves (with the same injury as the right side) were injected with vehicle alone (0.1% bovine serum albumin in PBS). Muscle incisions were sutured and the skin closed with metal clips. After recovery from the anesthetic, animals were returned to standard housing. Two days (for crush injury) and four days (for transection injury) after surgery, nerves were removed under anesthesia and fixed as described below. One of the eight animals receiving nerve transection and repair was excluded because loss of continuity in one nerve occurred during convalescence.

Preparation of acellular nerve grafts treated with chondroitinase. Adult (180–200 g) female SPRAGUE DAWLEY rats (HARLAN, Indianapolis, Ind.) were used as nerve donors and recipient hosts. Donor rats were anesthetized with halothane and decapitated. Sciatic nerves were exposed through a gluteal muscle-splitting incision and isolated free of underlying fascia. A 15-mm nerve segment was excised rostral to the bifurcation into common peroneal and tibial nerves. The segments were rinsed with cold sterile Ringer's solution, stabilized by pinning the ends to a thin plastic support, and transferred to a cryogenic vial. The vials were submerged in liquid nitrogen for 2 minutes and then transferred to a 37° C. water bath for 2 minutes. This freeze/thaw cycle was repeated, yielding acellular nerve grafts that were then stored in liquid nitrogen. On the day before grafting, the nerve grafts were warmed to room temperature and incubated in 100 $\mu$l phosphate buffered saline pH 7.4 (PBS) containing 2 units/ml chondroitinase ABC (SIGMA, St. Louis, Mo.) or in PBS (vehicle) only for 16 hours at 37° C. The grafts were rinsed twice with Ringer's and kept on ice prior to use. The chondroitinase ABC preparation was highly purified and stated by the manufacturer to be essentially free of protease activity.

Interpositional nerve grafting for chondroitinase experiments. Twelve rats received bilateral acellular nerve grafts, one chondroitinase-treated and one vehicle-treated graft. Host rats were deeply anesthetized using xylazine (15 mg/kg, i.m.) and ketamine (110 mg/kg, i.p.). The sciatic nerve was exposed and supported by a plastic insert placed between the nerve and underlying tissue. The region of nerve halfway between the sciatic notch and bifurcation was first coated with fibrin glue. Using serrated scissors, a 2.5-mm segment of host nerve was excised and replaced with a freshly trimmed 10-mm acellular nerve graft. The graft was coapted to the host nerve stumps by epineurial neurorrhaphy using one 9-0 ETHILON suture at each end. Fibrin glue was then applied to stabilize the coaptations which, in combination with the initial fibrin coating, also reduced protrusion of nerve elements (endoneurial mushrooming) (Menovsky T et al. [1999] *Neurosurgery* 44:224–226). The muscle was closed with 4-0 sutures and the skin with wound clips. After recovery from the anesthetic, animals were returned to standard housing.

Nine rats were terminated at 8 days and four at 4 days after grafting. Animals were deeply anesthetized and decapitated. The graft and 3 mm of proximal and distal host nerve were removed, immersed in 4% paraformaldehyde in 0.1 M phosphate buffer (pH 7.4) overnight at 4° C. The specimens were equilibrated with PBS and immersed in 30% sucrose/phosphate buffer for 2 days at 4° C. Using a dissecting microscope and the epineurial sutures as landmarks, each specimen was subdivided into 3 segments representing a) the proximal nerve-graft interface, b) the main graft and c) the distal nerve-graft interface. The specimens were embedded and cryosectioned. Longitudinal sections were taken through the nerve-graft interfaces to examine the continuity of the coaptations.

The main grafts were sectioned serially on the transverse plane in recorded measure to assess the extent of axonal growth by microscopy. Regenerating axons were labeled by GAP-43 immunofluorescence (see below) in sections of the grafts at 0.56 mm intervals. Epifluorescent photomicrographs were acquired using a SPOT Digital Camera System (DIAGNOSTIC INSTRUMENTS, INC., Sterling Heights, Mich.) and AXIOVERT 10 microscope (CARL ZEISS, Thornwood, N.Y.). GAP-43-positive axon profiles were scored using IMAGE-PRO PLUS software (MEDIA CYBERNETICS, Silver Springs, Md.).

Nerve explant culture for predegeneration experiments. Adult (180–200 gm) female SPRAGUE DAWLEY rats (HARLAN, Indianapolis, Ind.) were used as nerve donors and graft recipients. This project was reviewed and approved by the Institutional Animal Care and Use Committee. Donor rats were deeply anesthetized with isofluorane and decapitated. Sciatic nerves were exposed through a gluteal muscle-splitting incision and isolated free of underlying fascia. A 15-mm nerve segment was excised rostral to the bifurcation into common peroneal and tibial nerves. The segments were rinsed with sterile Ringer's solution and stabilized by pinning the ends to a thin plastic support. The nerve explants were cultured for 1, 2, 4 and 7 days in DULBECCO'S modified EAGLES' medium containing N2 supplements (DMEM/N2) or DMEM/N2 supplemented with 2% or 10% fetal bovine serum (FBS) (ATLANTA BIOLOGICALS, Atlanta, Ga.). As specified, some explants were cultured in the presence of the MMP inhibitor, GM6001 (50 $\mu$M) (Grobelny et al. [1992] *Biochem.*, 31:7152–7154). The cultured nerves were washed thoroughly in DMEM and then transferred to sealed tubes. The tubes were immersed in liquid nitrogen for 2 min and then thawed in a 37° C. water bath for 5 min. This freeze-thaw cycle was repeated twice, yielding freeze-killed (acellular) nerve segments. Freshly excised nerves (uncultured controls) were freeze-killed using the same procedure. The acellular nerve segments were then a) embedded for cryosectioning for use in cryoculture assays or b) stored in liquid nitrogen (for up to 2 weeks) for biochemical analysis and for use as interpositional nerve grafts. Nerve explants prepared for histological examinations were fixed with aldehydes and freeze-killing was omitted.

Nerve degeneration in vivo was accomplished by a single transection of the sciatic nerve near the pelvis. The proximal stump was displaced and ligated to preclude axonal growth. The leg muscles and skin were closed and the transected nerve was allowed to degenerate in situ for 2 or 7 days.

Immunocytochemistry. Axonal regeneration was assessed by GAP-43 immunofluorescence and digital image analysis. Tissue sections mounted on slides were washed with PBS and then treated with 0.5% Triton X-100 in PBS for 10 min. The sections were treated with blocking buffer (10% serum in PBS +0.1% Triton X-100) and then incubated overnight at 4° C. with primary antibodies (diluted in blocking buffer). Bound antibodies were labeled with swine anti-rabbit immunoglobulins (DAKO CORPORATION, Carpinteria, Calif.) or goat anti-mouse immunoglobulins (Sigma) FITC-conjugated secondary antibodies for 1 h at room temperature in darkness. The anti-mouse secondary antibody was preadsorbed with rat serum prior to use. The sections were washed, postfixed with 4% paraformaldehyde in PBS, rinsed, and coverslipped in fluorescent mounting media. Affinity-purified rabbit anti-GAP-43 peptide antibody was produced using known methods (Ferguson T A et al. [2000] *Mol Cell Neurosci*, 16:157–167) and was used at 2 $\mu$g/ml. Polyclonal antibody 1918 (CHEMICON INTERNATIONAL, Temecula, Calif.) (1:1000) binds only to the unsaturated disaccharide unit that remains attached to the linkage region of CSPG core protein exposed by digestion with chondroitinase ABC (Bertolotto A et al [1986] *J Neurol Sci* 73:233–244). Polyclonal anti-EHS laminin antibody (Sigma) (1:1000) was used to label basal laminae. Polyclonal anti-S-100 antiserum (Dako) (1:500) was used to label Schwann cells. Dark-field images were inverted and optimized for printing in PHOTOSHOP (ADOBE SYSTEMS INC., San Jose, Calif.).

Cryoculture bioassay. Cryoculture is a neurite outgrowth assay in which neurons are cultured directly on fresh/frozen nerve sections and was performed as described previously (Ferguson T A et al. [2000] *Mol Cell Neurosci*, 16:157–167). Briefly, chondroitinase- and vehicle-treated nerve segments were sectioned at 20 $\mu$m, mounted on sterile, aminopropyltriethoxysilane (APTS)-coated coverslips and stored at −20° C. until used. Where indicated, sections were treated with chondroitinase ABC (0.1 unit/ml) or vehicle (50 mM Tris-HCl, pH 8.0), containing 50 mM NaCl) for 2 h at 37° C. Purified dorsal root ganglionic (DRG) neurons from day 8 chick embryos were seeded directly on the nerve sections in a defined N2 medium (Bottenstein J E et al. [1980] *Exp Cell Res* 125:183–190) containing 10 ng/ml nerve growth factor. Cryoculture assays were terminated after 24 h of incubation by fixation with 100% methanol. Neuritic growth by DRG neurons was accessed by GAP-43 immunofluorescent labeling. Epifluorescent photomicrographs were acquired as described for tissue sections. Neurite lengths were measured directly using IMAGE-PRO PLUS software (MEDIA CYBERNETICS, Silver Springs, Md.). At least 250 neurons with neurites greater than one cell body (~15 $\mu$m) were scored for each condition in each experiment.

Gel zynography for nerve predegeneration experiments. Nerve segments were placed in ice-cold extraction buffer (50 mM Tris-HCl, pH 7.6, containing 1% Triton X-100, 200 mM NaCl, and 10 mM $CaCl_2$) and homogenized by probe sonication (15 sec). The samples were agitated for 30 min at 4° C. and the soluble fraction collected by centrifugation (12,000 g, 20 min). Total protein content of the soluble fractions was determined using the BRADFORD REAGENT (BIO-RAD LABORATORIES, Hercules, Calif.). Bovine serum albumin dissolved in extraction buffer was used as a protein standard. The extracts were solubilized in non-reducing Laemmli sample buffer without heating and electrophoresed at 4° C. on 10% SDS-polyacrylamide gels containing 1.5 mg/ml porcine gelatin. The gels were briefly rinsed in water and then washed in 2.5% Triton X-100 three times over 45 min. The Triton was removed with three 5-min water washes and the zymographic gels were developed for 21 h in incubation buffer (50 mM Tris-HCl, pH 8.0, 5 mM $CaCl_{2, 0.02}$% sodium azide). Gels were fixed and stained with 0.05% Coomassie brilliant blue. Protein bands with gelatinolytic activity appeared as a clear lysis zones within the blue background of the gelatin gel. Comigration of gelatinolytic bands was compared with latent and activated forms of recombinant human MMP-2 and MMP-9, as well as prestained molecular weight standards (BIO-RAD). Digital photomicrographs were acquired and densitometry of gelatinolytic bands was performed using IMAGE-PRO PLUS software.

In situ zymography for nerve predegeneration experiments. Cryosections (10 μm) of unfixed normal and cultured nerves were mounted on slides and overlaid with reaction buffer (50 mM Tris-HCl, 150 mM NaCl, 5 mM $CaCl_2$, 0.2 mM sodium azide, pH 7.6) containing 20 μg/ml of intramolecularly quenched, fluorescein-labeled gelatin substrate (MOLECULAR PROBES INC., Eugene, Oreg.) (Oh et al., 1999). In the control condition, the MMP inhibitor EDTA (30 mM) was included in the reaction buffer. After incubation for 24 h at 37° C., the sections were rinsed with PBS and fixed with 4% paraformaldehyde in phosphate buffer. The sections were rinsed with water and mounted using Citifluor. Fluorescein-gelatin peptides generated by gelatinolytic activity in the tissue sections were observed and photographed by epifluorescence microscopy.

Interpositional nerve grafting for predegeneration experiments. Six rats were given bilateral acellular nerve grafts, one normal (uncultured) and one predegenerated in vitro (cultured for 2 d in 2% serum). Host rats were deeply anesthetized using xylazine (15 mg/kg, i.m.) and ketamine (110 mg/kg, i.p.). The sciatic nerve was exposed and supported by a plastic insert placed between the nerve and underlying tissue. The region of the nerve halfway between the sciatic notch and bifurcation was first coated with fibrin glue. A 2.5 mm segment of the host nerve was excised using serrated scissors. The graft was thawed and freshly trimmed to 10 mm with a scalpel blade. The graft was coapted to the host nerve stumps by epineurial neurorrhaphy using one 9-0 Ethilon suture at each end. Fibrin glue was then applied to stabilize the coaptations that, in combination with the initial fibrin coating applied to the host nerve, reduced protrusion of nerve elements (endoneurial mushrooming) (Menovsky and Bartels, 1999, *Neurosurgery*, 44:224–225, discussion pp. 225–226). The muscle was closed with 4-0 sutures and the skin was closed with wound clips. After recovery from the anesthetic, animals were returned to standard housing. Eight days after grafting the host rats were deeply anesthetized and decapitated. The graft and 3 mm of proximal and distal host nerve were removed and immersed in 4% paraformaldehyde in 0.1 M phosphate buffer, pH 7.4, overnight at 4° C. The specimens were equilibrated with PBS and immersed in 30% sucrose in phosphate buffer for 2 d at 4° C. The specimens were embedded and cryosectioned on the transverse plane in a recorded measure. Regenerating axons within the grafts were labeled by GAP-43 immunofluorescence (see below). Epifluorescent photomicrographs were acquired and GAP-43-positive axon profiles were scored using IMAGE-PRO PLUS software.

Immunofluorescent labeling for nerve predegeneration experiments. Fixed tissue sections were treated with 0.5% Triton X-100 in PBS for 10 min. Non-specific antibody binding was blocked by pretreatment with PBS containing 0.1% Triton X-100 and 10% normal serum (Blocking buffer). Primary antibodies were diluted in Blocking buffer and applied overnight at 4° C. Bound primary antibodies were labeled with swine anti-rabbit immunoglobulins (DAKO, Carpinteria, Calif.) or goat anti-mouse immunoglobulins (Sigma) conjugated with fluorescein or rhodamine for 1 hour at room temperature in darkness. The anti-mouse secondary antibody was pre-adsorbed with rat serum prior to use. Neurite length (cryoculture) and axonal regeneration (grafting) were assessed by immunolabeling with polyclonal anti-GAP-43 IgG (2 μg/ml) (Ferguson and Muir, 2000, *Mol Cell Neurosci*, 16:157–167) (NB300–143; NOVUS BIOLOGICAL, Littleton, Colo.). Other primary antibodies included: polyclonal anti-MMP-2 IgG (4 μg/ml) (MMP2/475; Muir, 1995); polyclonal anti-MMP-9 IgG (4 μg/ml) (AB19047; CHEMICON, Temecula, Calif.); polyclonal anti-S-100 antiserum (1:500)(DAKO) and; polyclonal OX42 antiserum (1:500)(SEROTEK, Raleigh, N.C.); and monoclonal anti-neurofilament IgG (4 μg/ml) (NAP4; Harris et al., 1993). In some instances, epifluorescent photomicrographs were inverted and contrast-enhanced for printing in PHOTOSHOP (ADOBE SYSTEMS, San Jose, Calif.).

Following are examples which illustrate procedures for practicing the invention. These examples should not be construed as limiting. All percentages are by weight and all solvent mixture proportions are by volume unless otherwise noted.

EXAMPLE 1

Degradation of CSPG by Treatment of Acellular Nerve Segments with Chondroitinase The purpose of this experiment was to determine if chondroitinase treatment effectively degraded CSPG throughout intact segments of acellular nerves. Segments of rat sciatic nerve (1.5 cm in length) were made acellular by repeated freeze-thaw cycles and then bathed en bloc in a chondroitinase ABC solution for 16 hours. CSPG degradation within the chondroitinase pretreated nerves was examined by immunolabeling with neoepitope antibody Ab1918. This antibody binds to an epitope created on the core protein after lysis of the chondroitin sulfate chains by chondroitinase ABC (Bertolotto et al. [1986] *J. Neurol Sci*, 73:233–244). Ab1918 immunostaining was intense throughout the entire pretreated nerve segment, as shown in FIG. 1A. Furthermore, the intensity of Ab1918 immunostaining was not increased by an additional post-treatment of the sections with chondroitinase, as shown in FIG. 1B. Ab1918 immunoreactivity was absent in acellular nerves not exposed to chondroitinase (not shown). These findings indicate that the en bloc chondroitinase treatment effectively permeated all nerve compartments and thoroughly degraded CSPG side-chains.

In normal nerve, CSPG and laminin are mainly colocalized in the nerve sheaths and basement membranes, including Schwann cell basal laminae (Zuo et al. [1998a] *J. Neurobiol.*, 34:41–54). Their distributions were unchanged after repeated freeze-thaw and there was no indication at the light microscopic level that en bloc chondroitinase treatment altered ECM structures, as shown in FIGS. 1A and 1C). The integrity of chondroitinase-treated acellular nerve segments was an important consideration for their subsequent use as nerve regeneration grafts. Accordingly, the structural integrity of the pretreated nerve segments after nerve grafting was also examined. The intensity and distribution of Ab1918 immunoreactivity (in regions of the grafts not infiltrated by host cells) was unchanged after 8 days in vivo, indicating the primary structure of Schwann cell basal laminae remained intact, as shown in FIG. 1D. Taken together, these results demonstrate that en bloc chondroitinase treatment of acellular nerve grafts effectively degraded CSPG without compromising the basal lamina scaffold or dislocating its laminin content.

EXAMPLE 2

Inactivation of Inhibitory CSPG by Treatment of Acellular Nerve Segments with Chondroitinase Inactivation of inhibitory CSPG in chondroitinase-treated acellular nerve was determined by cryoculture bioassay. Embryonic chick DRG neurons were seeded onto sections of prepared nerve segments and the neurite-promoting activity was assessed by scoring neurite growth. Results are shown in FIG. 2. On sections of acellular nerve pretreated en bloc with vehicle only the average neurite length was 49 µm. Neurite growth on acellular nerve pretreated en bloc with chondroitinase averaged 96 µm, representing a 95% increase compared to the control condition. To determine if the en bloc chondroitinase treatment was thorough, cryoculture assays were performed on nerve tissues treated with chondroitinase after sectioning (post-treatment). As expected, the neurite-promoting activity of acellular nerve treated en bloc with vehicle only was increased significantly (86%) by post-treatment with chondroitinase. In contrast, chondroitinase post-treatment had only a slight additive effect on sections from en bloc chondroitinase-treated nerve grafts.

These results indicate that inhibitory CSPG was effectively degraded and inactivated by bathing segments of acellular nerve grafts in small amounts of chondroitinase ABC. In addition, en bloc chondroitinase treatment effectively deinhibited the nerve grafts without disrupting the laminin-associated, neurite-promoting potential of the basal lamina scaffold. The latter point was strengthened by the observation that, like in cryoculture assays of normal and degenerated nerve (Ferguson and Muir, 2000, Mol Cell Neurosci, 16:157–167), neurite growth on sections of chondroitinase-treated acellular nerve grafts occurred in strict association with Schwann cell basal laminae.

EXAMPLE 3

Figure 3:
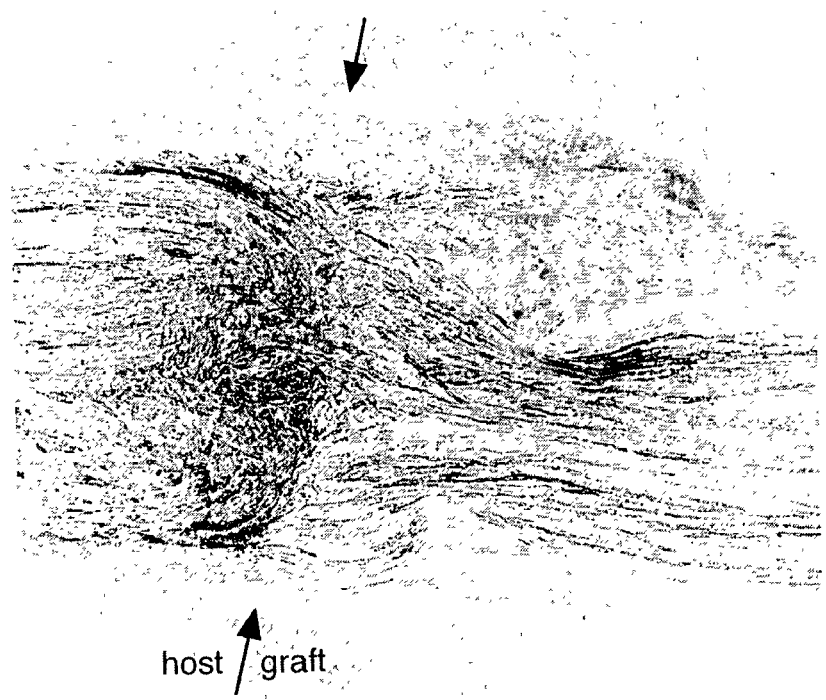
FIG. 3 shows an assessment of the continuity and GAP-43 immunostaining of interpositional acellular nerve grafts. The continuity of each nerve graft was confirmed by examining the proximal and distal nerve-graft coaptations in longitudinal section. At the proximal coaptation, GAP-43 labeling revealed numerous regenerating axons entering the proximal aspect of the graft. GAP-43 did not label any remnant elements within the acellular graft.
Figure 4:
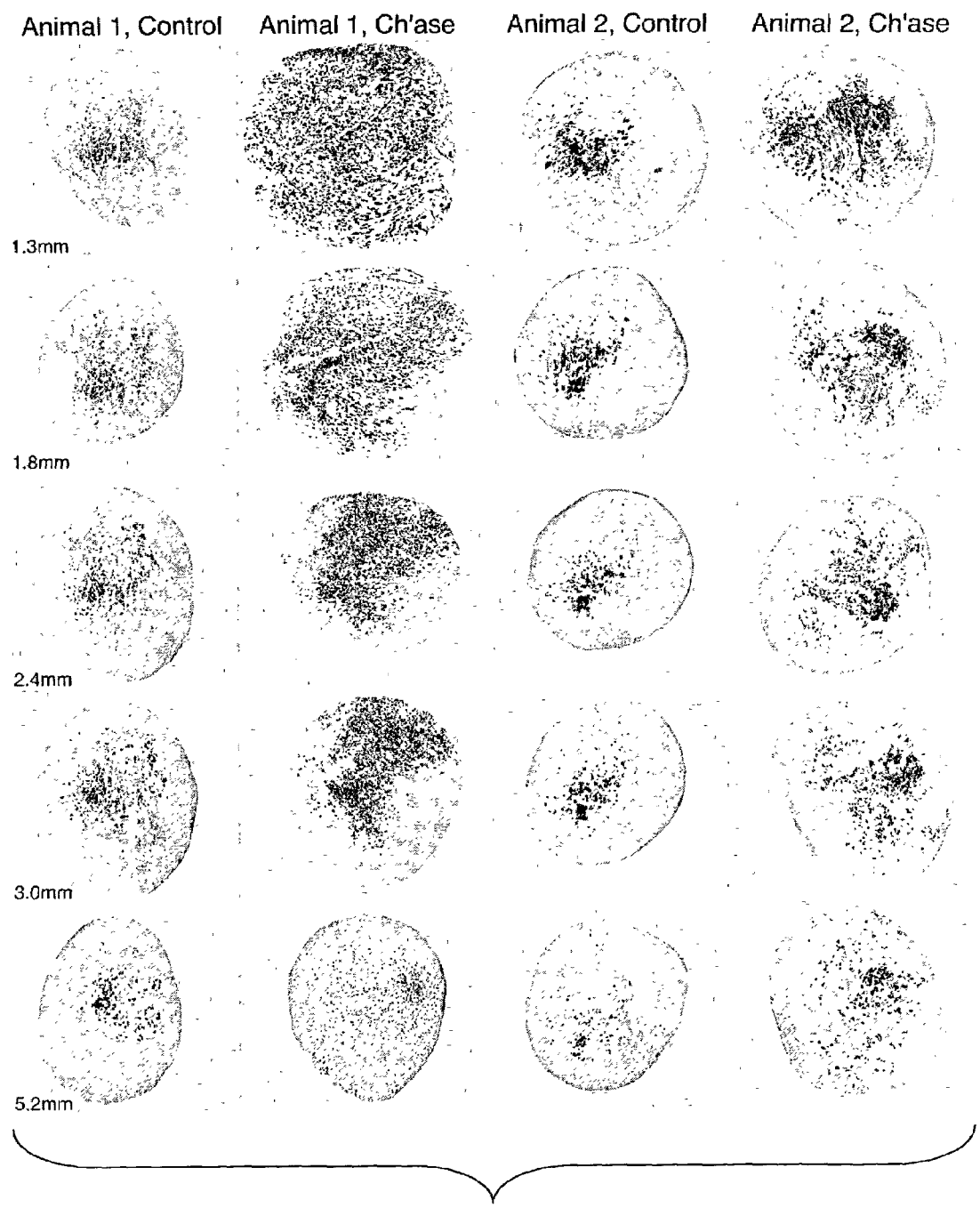
FIG. 4 shows axonal regeneration into acellular interpositional nerve grafts after 8 days. Representative series of sections from two animals, each receiving vehicle-treated and chondroitinase-treated grafts. Serial sections taken from the proximal graft (1.2 mm, top) and subsequent 0.56 mm intervals were immunolabeled with GAP-43. In each animal receiving bilateral grafts (n=9), axon growth was greater into the acellular graft treated with chondroitinase than in the vehicle-treated control. Images were cropped at the epineurium to approximate the fields scored by digital image analysis in FIG. 5.
Figure 5:
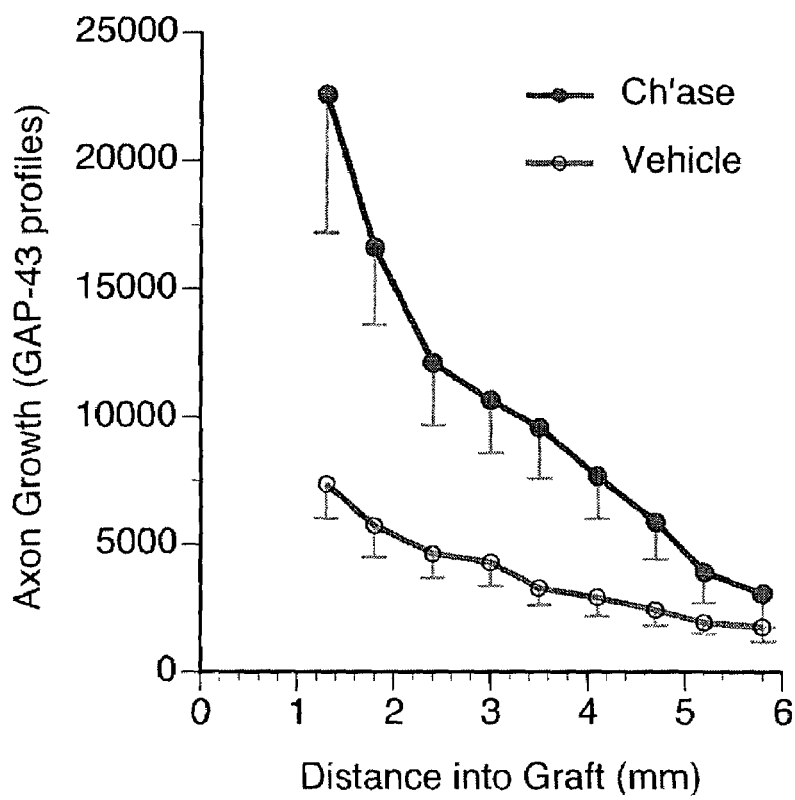
FIG. 5 shows greater accession of regenerating axons into chondroitinase-treated acellular nerve grafts. Serial sections of 8-day interpositional nerve grafts (as shown in FIG. 4) were scored for GAP-43-labeled axonal profiles by digital image analysis. Data represent the means (–SEM) of 9 vehicle-treated and 9 chondroitinase-treated grafts assessed at the specified distances into the graft (proximal to distal).

Nerve Regeneration is Enhanced by Chondroitinase Treatment of Acellular Nerve Grafts The following experiments tested the hypothesis that chondroitinase treatment improves nerve regeneration through acellular nerve syngrafts. As described in Example 2, acellular sciatic nerve segments were treated en bloc with vehicle or chondroitinase ABC. Ten-mm interpositional nerve grafts were joined to the host nerve by epineurial neurorrhaphy reinforced with fibrin glue. Each of nine host rats received bilateral grafts, one vehicle-treated and one chondroitinase-treated graft. Regeneration was initially examined after 8 days. First, the proximal and distal nerve-graft coaptations were examined in longitudinal section to assess the alignment of the surgical coaptation, as shown in FIG. 3. All of the grafts were in continuity and thus were included in the subsequent analysis. Scoring of regeneration was based on GAP-43-immunolabeling which intensely stained growing axons. Axon and Schwann cell remnants within the freeze-killed grafts were immunonegative for GAP-43 and host Schwann cells were only very faintly stained (at an intensity below the threshold used for digital scoring). Axonal growth was assessed at specified spatial intervals within the graft by scoring GAP-43-immunopositive profiles in transverse sections. Some axonal ingrowth was observed in all grafts, as shown in FIG. 4. However, the growth into chondroitinase-treated grafts was markedly greater and more widely distributed than in control grafts. Quantitative results are shown in FIG. 5.

The average number of axons (GAP-43-immunopositive profiles) entering chondroitinase-treated grafts was on average more than three-fold greater than in control grafts. While the axons entering the control grafts were always restricted and most often clustered centrally, the initial growth into chondroitinase-treated grafts was more widely dispersed and especially abundant at the proximal end. These findings indicate that the success of axonal penetration into acellular nerve grafts was markedly improved by pretreatment of the grafts with chondroitinase. However, a similar number of axons was consistently observed at the distal ends of grafts in both conditions. This suggested that axonal penetration into the control grafts occurred early and then was temporally restricted while axons continued to penetrate chondroitinase-treated grafts throughout the 8-day period.

Figure 6:
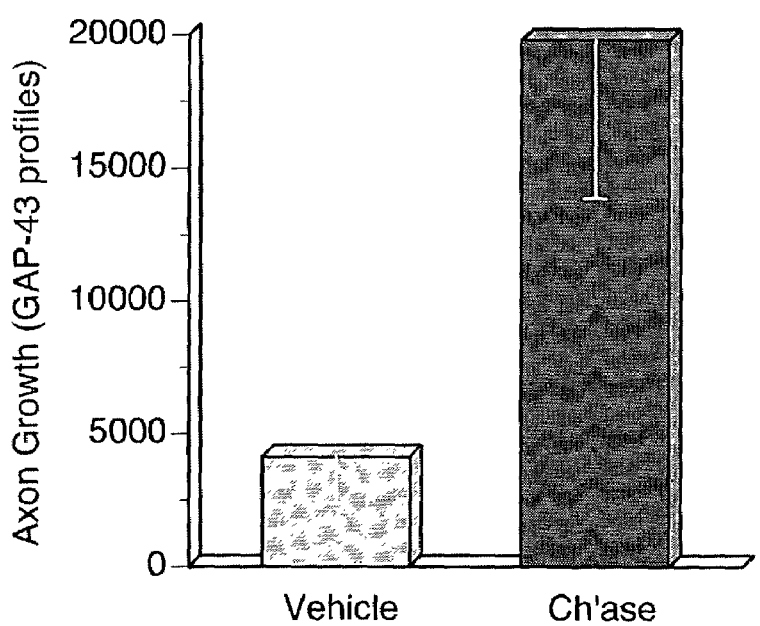
FIG. 6 shows axonal regeneration into the initial segment of acellular interpositional nerve grafts after 4 days. The nerve-graft interface and immediately proximal region of 4-day acellular grafts were examined. GAP-43-labeled axon profiles were compared at 0.3 mm into the grafts. Data represent the means (–SEM) of 3 vehicle-treated and 3 chondroitinase-treated grafts.

To determine if the latency of axonal growth into acellular grafts was reduced by chondroitinase treatment, the same analysis was performed on 4-day grafts except that the most proximal aspects of the grafts were examined and scored in transverse section as well. Although only 3 animals receiving bilateral grafts were examined, the results were consistent with those observed for 8-day grafts. Moreover, at the most proximal aspect of the graft (0.3 mm from the host-graft interface) axonal penetration was on average five-fold greater in chondroitinase-treated grafts, as shown in FIG. 6. From these results, it can be concluded that chondroitinase treatment decreases the latency and significantly improves the accession of axonal regeneration into acellular nerve grafts.

EXAMPLE 4

Axon Regeneration within Basal Lamina Tubes of Chondroitinase-Treated Grafts

Because the success of nerve regeneration depends on the growth of axons within the laminin-rich, basal lamina tubes, it was determined whether the association of axonal growth with basal laminae was altered by chondroitinase-treatment of acellular grafts. Transverse sections of 8-day grafts were double-labeled for GAP-43 and laminin. Laminin labeling was intense and basal laminae appeared similarly intact throughout control and chondroitinase-treated grafts. Despite repeated freeze-thaw, enzyme treatment, surgical manipulation and 8 days in vivo, the extracellular matrix scaffold appeared structurally intact. Multiple GAP-43 labeled axons (or neurites) were evident within individual basal laminae and the vast majority of these were observed in close association with the lumenal surface of the tubes. A similar and minor number of neurites with ambiguous apposition were observed in control and treated grafts. By and large, the propensity of axons to grow within basal laminae was unaltered by chondroitinase treatment of acellular nerve grafts.

EXAMPLE 5

Axonal Growth and Schwann Cell Migration into Chondroitinase-Treated Grafts

Figure 7:
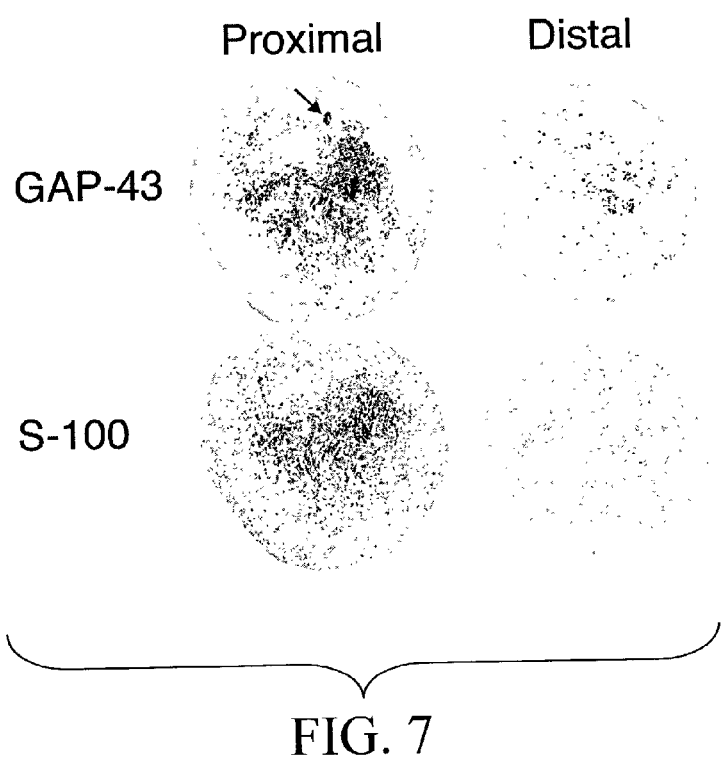
FIG. 7 shows the association of axon regeneration and Schwann cell migration within the grafts. Serial sections of 8-day grafts were immunolabeled for GAP-43 (axons) and S-100 (Schwann cells). In proximal regions of the chondroitinase-treated grafts, Schwann cells were most often found in close association with regenerating axons. Occasional clusters of axons were observed without comigrating Schwann cells (arrow). At more distal points in the grafts, axons were often found without accompanying Schwann cells. Few isolated Schwann cells were intensely immunolabeled for S-100 in the more distal regions of the grafts, which contained mostly faint S-100 staining associated with freeze-killed Schwann cell remnants.
Figures 8A, 8B:
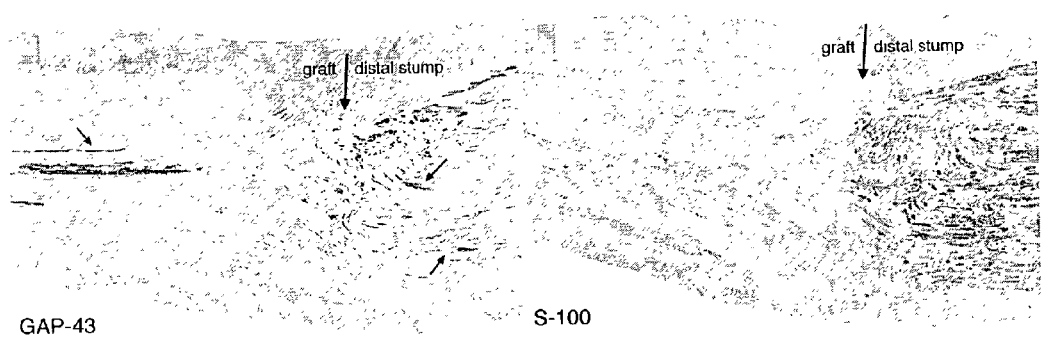
FIGS. 8A and 8B show axon and Schwann cell growth at the distal graft coaptation. Serial longitudinal sections of 8-day chondroitinase-treated grafts and distal nerve stumps were immunolabeled for GAP-43 (axons), as shown in FIG. 8A, and for S-100 (Schwann cells), as shown in FIG. 8B.

Serial sections of the 8-day grafts were immunolabeled for S-100 and GAP-43 to examine the migration of Schwann cells in respect to axon growth. The grafts contained two distinct patterns of S-100 staining; intense staining was associated with live, host-derived Schwann cells and faint staining with freeze-killed Schwann cell remnants. The descriptions that follow refer to the intensely stained (live) Schwann cell profiles, unless otherwise indicated. In proximal regions of the grafts the distributions of Schwann cells and axons mainly coincided, as shown in FIG. 7. Occasional clusters of axons were found without any apparent Schwann cell association. Scattered Schwann cells were also seen in regions without growing axons. Schwann cell migration was apparent well into the 8-day grafts. However, at more distal points in the grafts, axons were often found without accompanying Schwann cells, as shown in FIG. 7. This was confirmed in longitudinal sections including the distal coaptation, as shown in FIG. 8. S-100 labeled Schwann cells were abundant in the distal host stumps, yet few if any had invaded the distal aspect of the grafts (which contained only freeze-killed Schwann cell remnants), as shown in FIG. 8B. The examples presented in FIGS. 7, 8A, and 8B, were obtained from chondroitinase-treated grafts and identical results were observed in the control grafts. These findings suggested that the enhancement of axonal growth in chondroitinase-treated grafts was primarily attributed to the potentiation of the neurite-promoting activity of the basal lamina.

The path of axonal growth was examined only in longitudinal sections of tissues immediately surrounding the proximal and distal coaptations. Upon entering the grafts, axon growth was directed distally and there was no indication of deviant growth or neuroma formation within the grafts. This suggested that guidance mechanisms (or chemoattractant properties associated with the distal stump) were not compromised in chondroitinase-treated grafts. In addition, based on the few instances where axons had reached the distal extent of the graft, axons exited the grafts and continued growth into the host nerve stump, as shown in FIG. 8A.

EXAMPLE 6

Degradation and Inactivation of Inhibitory CSPG by Treatment of Acellular Human Nerve Segments with Chondroitinase Many of the experiments described in the examples above performed using rat nerves also have been replicated using human nerve. Except where otherwise indicated, the procedures described in Examples 1 and 2 using rat nerve were also followed in Examples 6 and 7 using human nerve. Human sural and tibial nerves were obtained fresh from surgical leg amputation. Amputations were necessary for diseases that did not have nerve involvement (e.g., bone cancer) and nerves were judged to be normal on the basis of histological examination.

Figure 9B:
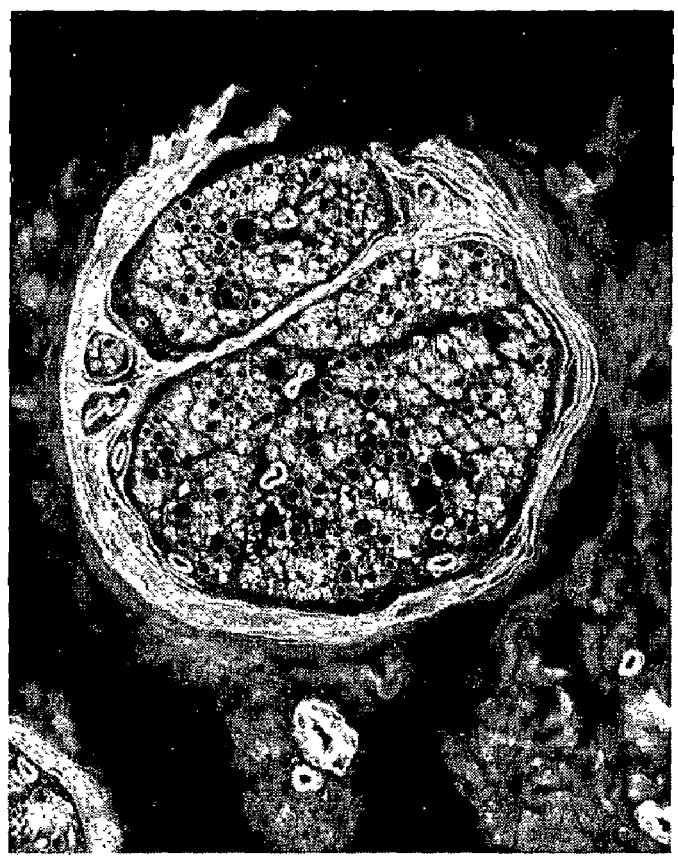
FIGS. 9A and 9B show human nerves stained for CSPG neoepitope and laminin, respectively. These results show that, although the gross structure of human nerve is more complex than rat nerve, the basal lamina which supports axon regeneration is mainly similar and the molecular components that regulate growth (CSPG and laminin) are abundant.
Figure 9A:
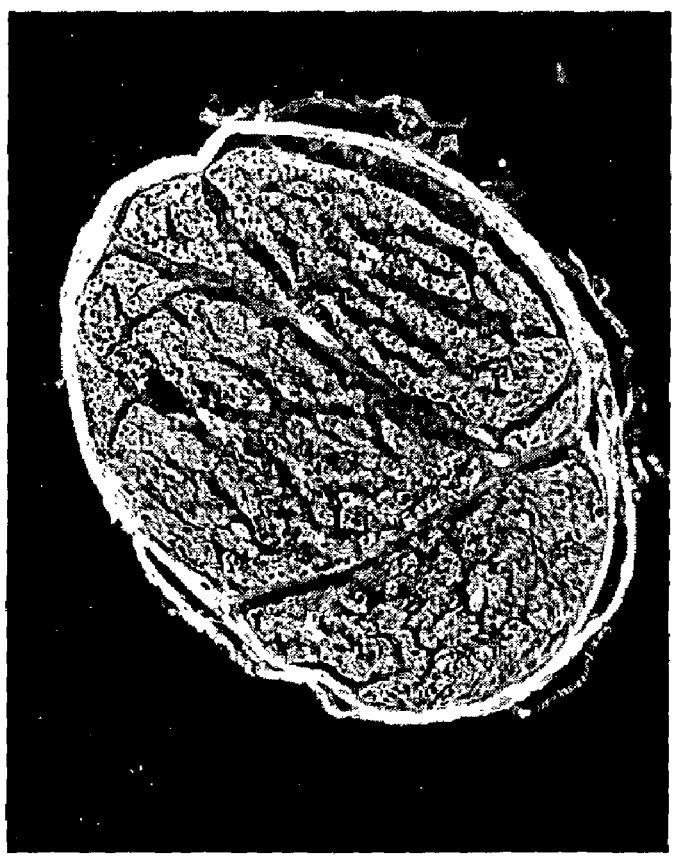
Figure 10:
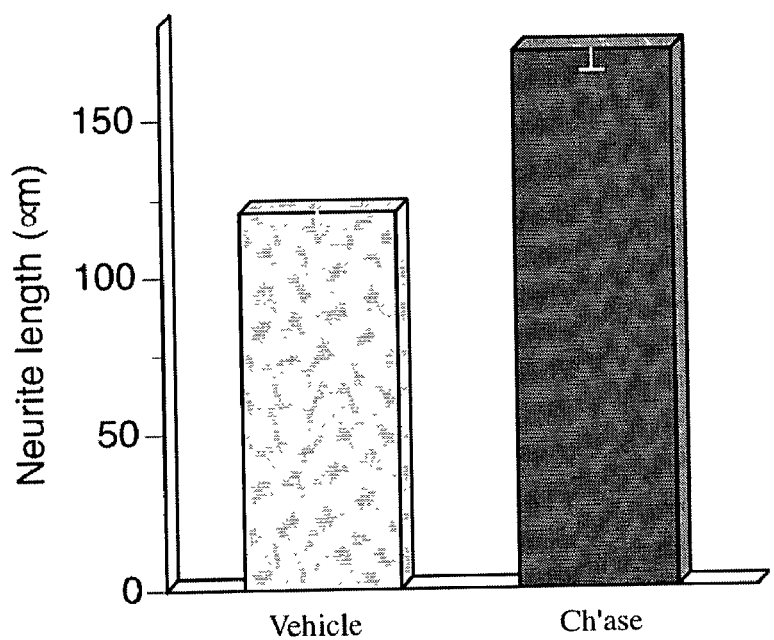
FIG. 10 shows inactivation of inhibitory CSPG by cryoculture assays using human nerve segments. Human nerves were treated with chondroitinase and then assayed for neurite-promoting activity. Dissociated chick DRG neurons were grown on the sections for 24 h and neurite lengths were scored. Results are expressed as means (–SEM). Statistical significance (P<0.001) comparing vehicle-treated and chondroitinase-treated conditions was found using Student's t test.

Human nerves were first examined to determine if their content of CSPG and laminin was similar to that observed in rat nerves. Immunocytochemistry showed that the basal lamina, which supports nerve regeneration, contained both CSPG and laminin, which are colocalized in the same fashion as in other species. Human nerves stained for CSPG neoepitope and laminin are shown, respectively, in FIGS. 9A and 9B. Furthermore, using the cryoculture bioassay, it was found that the growth-promoting properties of human nerves were increased by treatment with chondroitinase. Quantitative results are shown in FIG. 10.

EXAMPLE 7

Axon Regeneration within Chondroitinase-Treated Human Nerve Grafts

In the following experiments, the hypothesis that chondroitinase treatment improves nerve regeneration through acellular human nerve grafts in a rat xenograft model was tested. Subunits (individual fascicles) taken from human nerves were treated en bloc with vehicle or chondroitinase ABC. Ten-mm interpositional nerve grafts were joined to the rat host sciatic nerve by epineurial neurorrhaphy reinforced with fibrin glue. Each of 2 host rats received bilateral grafts, one vehicle-treated and one chondroitinase-treated graft. Regeneration was initially examined after 8 days. Axonal growth was assessed at specified spatial intervals within the graft by scoring GAP-43-immunopositive profiles in transverse sections.

Figure 11:
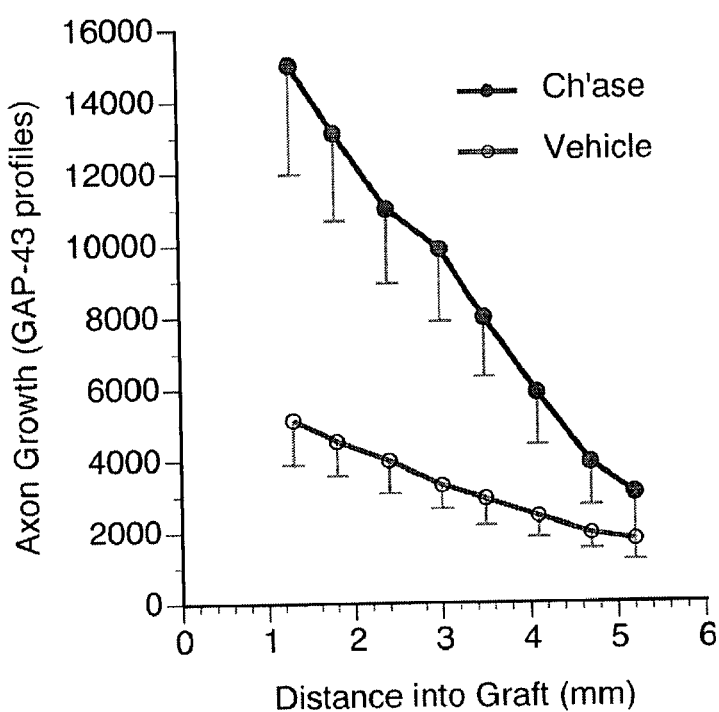
FIG. 11 shows greater growth of axons into chondroitinase-treated acellular nerve grafts in a human-to-rat xenograft model. Human nerve fascicles (of similar diameter to the rat sciatic nerve) were grafted into a gap made in the rat sciatic nerve. Serial sections of the 8-day interpositional nerve xenografts were scored for GAP-43-labeled axonal profiles by digital image analysis. Data represent the means (–SEM) of 2 vehicle-treated and 2 chondroitinase-treated grafts assessed at the specified distances into the graft (proximal to distal).

The growth into chondroitinase-treated grafts was markedly greater and more widely distributed than in control grafts. Quantitative results are shown in FIG. 11. The average number of axons (GAP-43-immunopositive profiles) entering chondroitinase-treated grafts was on average more than three-fold greater than in control grafts. These findings indicate that the success of axonal penetration into acellular human nerve grafts was markedly improved by pretreatment of the grafts with a CSPG-degrading enzyme. This xenograft model also demonstrates that acellular human nerves were not rejected (within 8 d) by the rat host, confirming the low immunogenicity of acellular nerves.

EXAMPLE 8

Degradation of CSPG in the Nerve after Chondroitinase Injection

Figures 12A, 12B, 12C, 12D:
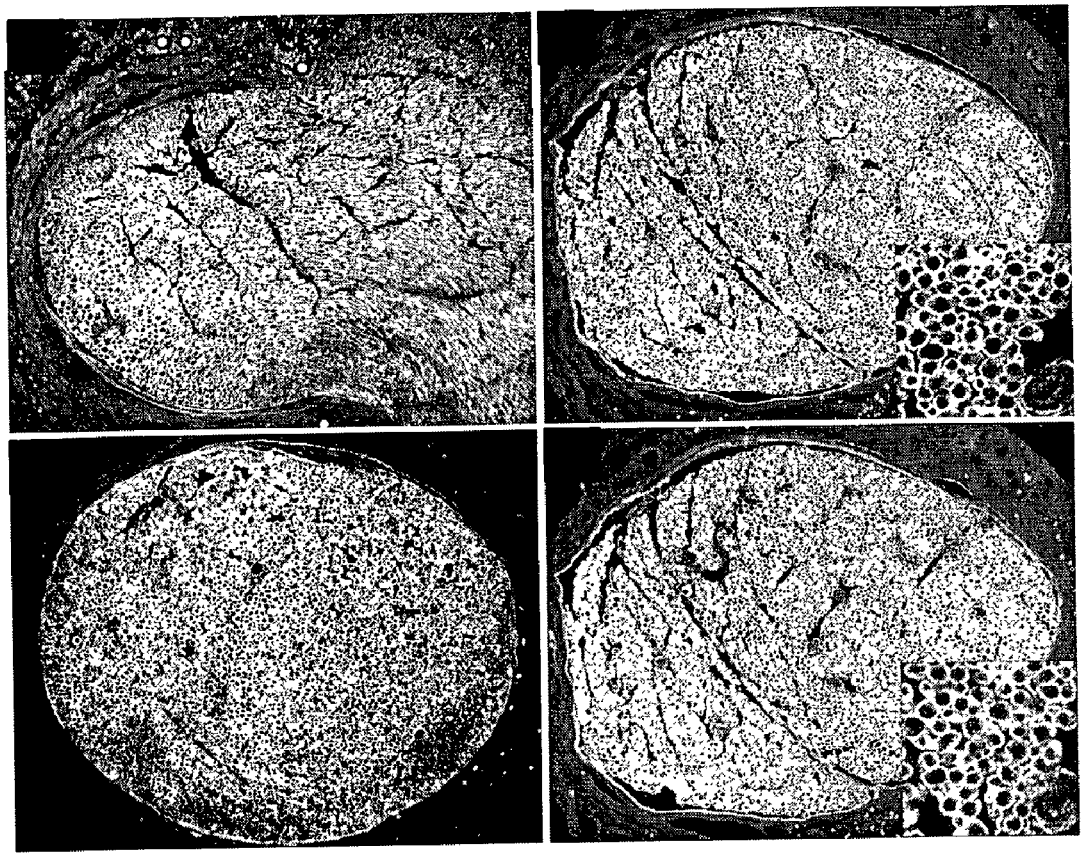
FIGS. 12A–12D show degradation of CSPG in the injured sciatic nerve by a single injection of chondroitinase ABC. Two injury models were examined, bilateral nerve transection and repair (FIGS. 12A, 12B, and 12D) and bilateral nerve crush (FIG. 12C). At the time of injury the right sciatic nerve was injected with chondroitinase ABC (1U in 2 µl) at a site 2 mm distal to the site of nerve injury. Four days after nerve transection and repair, CSPG-neoepitope immunostaining was intense throughout the endoneurium and nerve sheaths at the coaptation site (FIG. 12A) (note sutures in the epineurium) and throughout the cross-sectional area of the nerve several mm both distal (FIG. 12B) and proximal (not shown) to the coaptation.

Animals received either bilateral nerve crush injury or bilateral nerve transection and direct suture repair. At the same time, one nerve was injected with chondroitinase ABC and the contralateral nerve received vehicle alone. Whether the chondroitinase treatment effectively degraded CSPG in the injured nerves was first examined. Tissue sections of nerve at and surrounding the site of injury were immunolabeled using CSPG-neoepitope antibodies. These antibodies bind to new epitopes created on the CSPG core protein after lysis of chondroitin sulfate chains by chondroitinase ABC. In transected nerves four days after injury and chondroitinase application, CSPG-neoepitope immunostaining was intense at the coaptation and throughout the cross-sectional area of the distal nerve several mm peripherally, as shown in FIGS. 12A and 12B. Intense immunolabeling was also observed several mm into the proximal nerves. Similar results were obtained in crush-injured nerves, as shown in FIG. 12C. CSPG-neoepitope labeling of tissue near the coaptation and injection site was at most marginally more intense when a secondary treatment with chondroitinase was applied to the tissue sections as part of the immunostaining procedure, as shown in FIG. 12D. These results indicate that in vivo treatment with chondroitinase ABC substantially, if not completely, degraded CSPG in the extracellular matrix surrounding the site of injection, including the site of nerve injury and repair.

EXAMPLE 9

Chondroitinase Treatment Did Not Alter Axonal Regeneration After Nerve Crush Injury (Axonotmesis)

The hypothesis that chondroitinase treatment improves axonal growth through the site of nerve crush injury was tested. Bilateral axonotmesis was achieved by severely crushing the sciatic nerves while maintaining the continuity of the nerve sheaths. At the time of injury, one nerve was injected with chondroitinase ABC and the contralateral nerve received vehicle alone. Because of the rapid regrowth of axons after nerve crush, axonal growth across the injury site was examined two days after injury. Regenerating axons were labeled by GAP-43 immunofluorescence and scored by digital image analysis. As expected in control nerves, axonal regeneration directly distal to the crush site was robust and widespread throughout the nerve cross-section, as shown in FIG. 13A. A similar regenerative response and growth pattern was observed in the chondroitinase-treated nerves as well. In both conditions, immunolabeling was very dense and numerous neurites were seen within each basal lamina tube. Quantitative assessment of GAP-43 immunoreactivity showed that axonal regeneration after nerve crush injury was not significantly effected by chondroitinase application (FIG. 13B). Likewise, there was no indication that the latency or rate of axonal regeneration was altered in the chondroitinase-treated nerves.

EXAMPLE 10

Regeneration of Axons after Nerve Transection (Neurotmesis) Repair is Enhanced by Chondroitinase Treatment The hypothesis that chondroitinase treatment improves axonal growth through the site of nerve coaptation was tested. Bilateral neurotmesis was achieved by a scissor cut of the sciatic nerves which were then repaired by epineurial suture and fibrin glue. One nerve was injected with chondroitinase ABC and the contralateral nerve received vehicle alone. Because of the latency of regeneration after nerve transection, axonal growth across the coaptation was examined four days after injury. In control nerves, the ingress of axons occurred mainly in patches and was limited to discrete subsections of the distal nerve; otherwise only a few axons were found scattered throughout the remaining nerve cross-section, as shown in FIG. 14A. The number of axons extending farther into the distal (after 4 days) rapidly diminished and approached zero within 3 mm from the coaptation. In contrast, axon ingress into chondroitinase-treated nerves was more robust and widespread throughout the entire nerve cross-section. In 7/7 animals, the number of axons that entered the distal nerve was greater in the chondroitinase-treated nerve than in the control nerve. On average, the score of axons immediately distal to the coaptation was two-fold greater in the chondroitinase-treated nerves, and 3/7 animals had increases greater than 3.5-fold, as shown in FIG. 14B. The ratio of axon numbers in chondroitinase-treated compared to control nerves progressively increased from 2:1 (just beyond the coaptation) to more than 4:1 at points farther into the distal stump. Thus, in addition to increasing the number of axons invading the distal nerve, chondroitinase treatment also decreased the latency of axonal ingress and/or increased the rate of growth within the distal nerve segment. It was clear that axon growth in all portions of the distal nerve was strictly linear and aligned with the longitudinal axis of the nerve. In addition, double-immunolabeling for regenerating axons (GAP-43) and basal laminae (laminin) indicated that the strong propensity of axons to regrow within basal laminae of the distal nerve was unaltered by chondroitinase treatment.

These findings show that axonal regrowth after crush injury was similar in chondroitinase-treated and control nerves. In contrast, axonal regrowth through the coaptation of transected nerves was accelerated and the ingress of axons into the distal segment was increased several-fold in nerves injected with chondroitinase. Thus, in transection injury when nerve continuity is disrupted, chondroitinase application significantly increased the ability of axons to access basal laminae of the distal nerve segment and markedly enhanced regeneration.

In accordance with the subject invention, a single injection of chondroitinase can markedly improve axonal regeneration across the interface of coapted peripheral nerve. Degradation of inhibitory CSPG creates a more permissive nerve substratum and allows axon sprouts greater latitude in their effort to locate and access Schwann cell basal laminae of the distal nerve. The difficulty that axons face in this process is evidenced by the increased latency associated with regeneration after transection injury as compared to crush injury. Notably, the data suggest that an important effect of chondroitinase treatment is to decrease the latency of regeneration in the peripheral nerve transection model. In addition, it is known that axonal sprouts will degenerate if they fail to traverse the coaptation (Fu, S. Y., and T. Gordon 1997, *Mol Neurobiol* 14: 67–116).

EXAMPLE 11

The Neurite-Promoting Activity of Cultured Nerve Segments

Figures 15A, 15B:
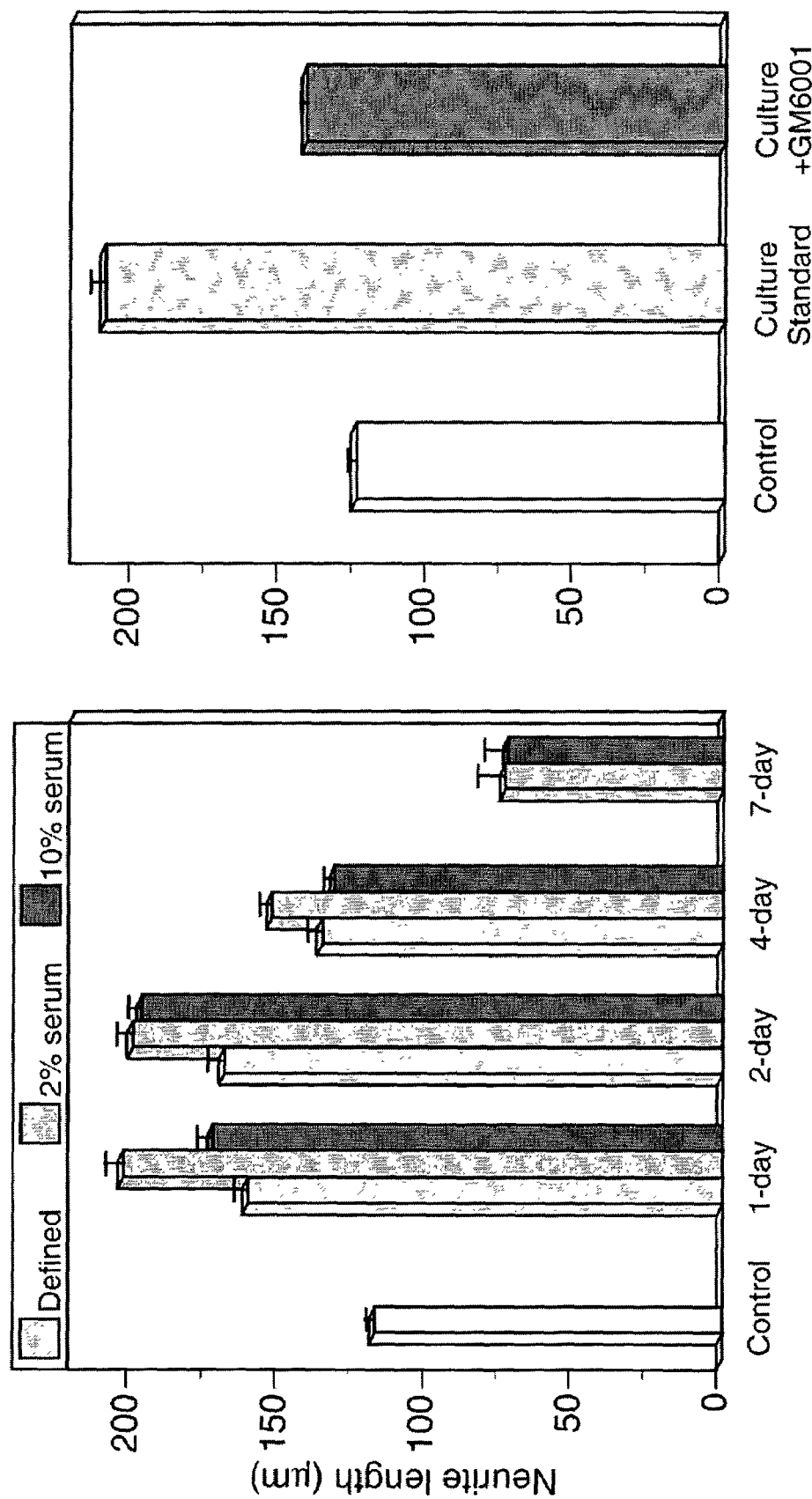
FIGS. 15A and 15B show the cryoculture assay of nerve explant cultures.

Freshly excised (cellular) rat sciatic nerve segments were cultured for up to 7 days in medium containing 0, 2 and 10% fetal bovine serum. Control (uncultured) and cultured nerves were cryosectioned and their neurite-promoting activity was assessed by cryoculture assay. Results are shown in FIG. 15A. Embryonic chick DRG neurons grown on sections of control nerves had an average neurite length of 118 $\mu$m. Neuritic growth on sections of nerve explants cultured for 1–4 days was significantly greater. For nerves cultured in defined medium (0% serum), neurite-promoting activity reached a maximum at 2 days in vitro, representing a 43% increase compared to control nerves. There was more than a 70% increase in the neurite-promoting activity for nerve explants cultured for 1 or 2 days in medium containing 2% serum. Nerve explants cultured in 10% serum reached a similar maximum at 2 days in vitro as well. The neurite-promoting activity of nerves explants declined after longer culture periods and fell below the level of the control condition at 7 days. These data indicate that the neurite-promoting activity of nerve explants increased markedly when cultured for short periods in vitro with and without the addition of serum to the culture medium. Nerve explants were prevented from adhering to the culture vessel and no cell outgrowth was observed. However, cell viability in all conditions was confirmed in separate experiments in which robust cell migration was observed from nerve explants that were minced and pressed to the culture surface.

EXAMPLE 12

Comparison of In vitro and In vivo Predegeneration

Using the cryoculture assay, the neurite-promoting activity of rat sciatic nerves predegenerated in vitro was compared to those predegenerated in vivo. As described above (see FIGS. 15A and 15B), neuritic growth of DRG neurons on nerve explants cultured for 2 days in 2% serum (in vitro predegeneration) was 70% greater than control nerves (not predegenerated). Also, nerve explant culture for longer periods (4 and 7 days) resulted in a progressively less neurite-promoting activity. Nerves cultured for 7 days had 37% less activity than the control condition. By comparison, the neurite-promoting activity of nerves predegenerated in vivo was much lower those predegenerated in vitro. Neuritic growth on nerves predegenerated in vivo for 2 days was 35.8 $\mu$m, 72% less activity than the control condition (126.5 $\mu$m) (t-test, p<0.001). However, this inhibition was reversed over time and in vivo predegeneration for 7 days resulted in neuritic growth 12% greater than the control condition (p=0.06). These data show that in vitro predegeneration increased the neurite-promoting activity of nerve segments to a greater extent than that achieved by in vivo predegeneration.

EXAMPLE 13

In vitro Degeneration is MMP-Dependent

Nerve segments were cultured for 2 days in medium containing 2% serum with and without the addition of the MMP inhibitor, GM6001. The neurite-promoting activity of the cultured nerves was assessed by cryoculture assay. Results are shown in FIG. 15B. Similar to that shown in FIG. 15A, the mean neurite length of DRG neurons grown on cultured nerves (2-day, 2% serum) was 210 $\mu$m, representing a 68% increase over that of (uncultured) control nerves. However, this increase was reduced to only 14% for nerves cultured in the presence of GM6001. Dissociation culture (squash preparations) of the nerve segments in each condition showed profuse cell outgrowth indicating no loss of cell viability. In addition, treatment of isolated Schwann cell cultures with GM6001 confirmed the very low toxicity of this hydromate-based dipeptide. These results strongly implicate MMP activity in a degenerative process that increases the neurite-promoting activity of cultured nerve explants.

EXAMPLE 14

MMP Expression in the Cultured Nerve Segments: Zymographic Gel Analysis

Figure 16:
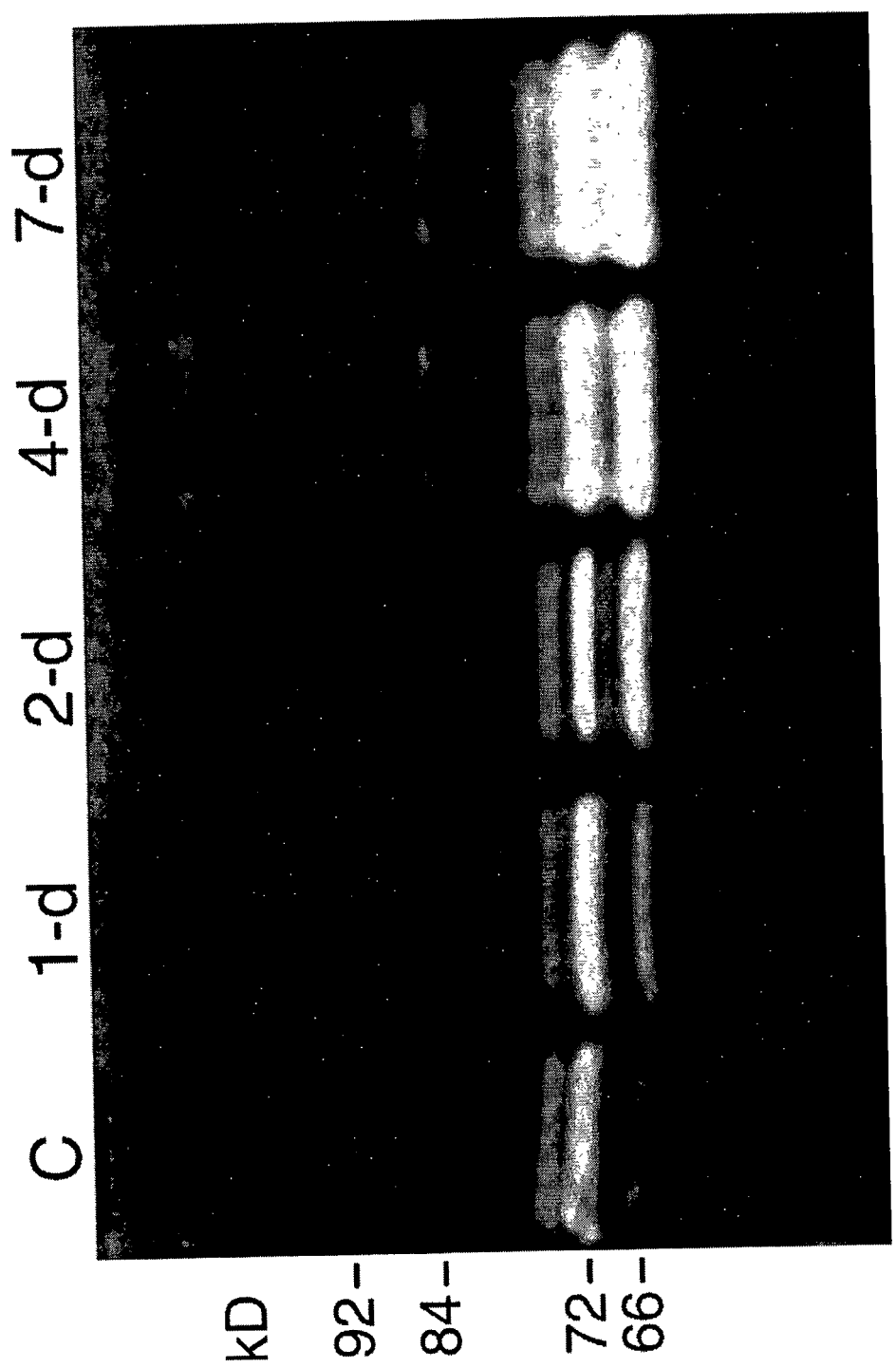
FIG. 16 shows the zymographic analysis of nerve explant cultures. Nerve explants were cultured for 0 (Control, C), 1, 2, 4, and 7 days in DMEM/N2 containing 2% serum. The nerves were then extracted and analyzed by gelatin-overlay electrophoresis. Zymography reveals both proform and activated gelatinases which appear as clear bands within the stained gel. Control nerve contained predominantly pro-MMP-2 and trace amounts of activated MMP-2. There was a progressive increase in MMP-2 content and a rapid conversion to the activated form within the nerve explants cultured for 2 days or longer. MMP-9 was negligible in the control and early explants whereas a trace amount was detected at 4 and 7 days. The molecular masses indicate the positions of recombinant human pro-MMP-9 (92 kD), activated MMP-9 (84 kD), pro-MMP-2 (72 kD) and activated MMP-2 (66 kD).

MMP-2 and MMP-9 are the main extracellular proteinases capable of degrading gelatin (cleaved collagen) and their major substrate is collagen type IV of the basal lamina. MMP-2 is constitutively expressed by Schwann cells in vivo and is upregulated after nerve injury in the rat. On the other hand, MMP-9 is undetectable in normal nerve and is present after injury in association with invading granulocytes and macrophages. Examination of in vitro nerve degeneration in the present invention provides a unique opportunity to determine the role of MMP expression by resident nerve cells with a minimal contribution by hematogenic cells. MMP levels in cultured nerve explants were first examined by gelatin substrate-overlay gel electrophoresis (zymography). Gelatin zymography is very sensitive in the detection of MMP-2 and MMP-9 and has the added advantage of revealing both latent and activated forms. Nerve segments were cultured for 1, 2, 4 and 7 days in the presence of 2% serum A representative zymographic analysis of extracted nerves is shown in FIG. 16. Normal (uncultured control) nerve showed a predominant gelatinolytic band at $M_r$=72 kD that comigrated with the proform of human recombinant MMP-2. A trace of activated MMP-2 was observed ($M_r$=66 kD), whereas MMP-9 ($M_r$=92 and 84 kD) was not detected. In the cultured nerves, there was a rapid increase in activated MMP-2 and a substantial increase in total MMP-2 content. MMP-9 was undetectable in nerves cultured for 1 or 2 days and trace amounts of activated MMP-9 in the 4- and 7-day samples. Similar results were obtained for nerve explants cultured in defined medium, confirming that serum did not contribute to the gelatinolytic activity observed in the nerve samples. These findings indicate that MMP-2 is rapidly activated and upregulated in nerve degeneration in vitro. It is notable that gelatin zymography is several-fold more sensitive in detecting MMP-9 than MMP-2 (Ladwig et al. [2002] *Wound Repair Regen* 10:26–37), signifying that MMP-9 content in the nerve samples was negligible.

EXAMPLE 15

MMP Activity in the Cultured Nerve Segments: in situ Zymography

Figures 17A, 17B, 17C, 17D, 17E, 17F:
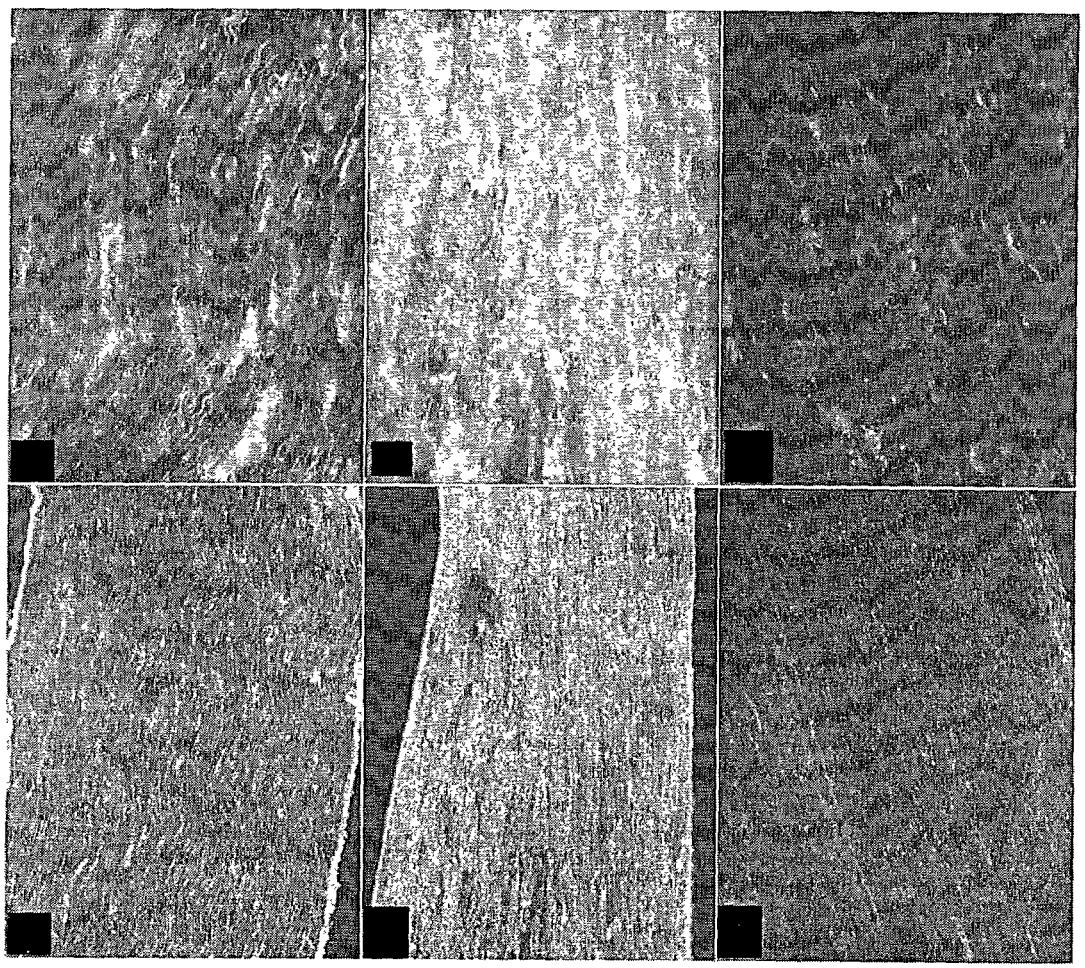
FIGS. 17A–17F show the localization of net gelatinolytic activity in nerve segments by in situ zymography. Tissue sections of control nerve (FIG. 17A and FIG. 17B) and cultured nerve explants (2-day, 2% serum) (FIG. 17C and FIG. 17D) were overlaid with quenched, fluorescein-labeled gelatin, which is converted to fluorescent peptides by gelatinolytic activity within tissues. Constitutive gelatinolytic activity was detected in normal nerve (FIG. 17A) which, at higher magnification (FIG. 17B), was associated with Schwann cells.

The activity of MMPs is regulated by gene transcription, proenzyme activation and by the action of tissue inhibitors of metalloproteinases. The net gelatinolytic activity in nerve segments by in situ zymography was examined. Tissue sections were overlaid with quenched, fluorescein-gelatin, which is converted to fluorescent peptides by gelatinolytic activity within tissues. Constitutive gelatinolytic activity was detected in normal nerve mostly associated with Schwann cells aligned along the endoneurial basal lamina (as shown in FIGS. 17A and 17B). In cultured nerves there was widespread increase in gelatinolytic activity that was diffuse within the endoneurium and Schwann cells were labeled more intensively, as shown in FIGS. 17C and 17D. Also examined, was the gelatinolytic activity in the nerves cultured in the presence of GM6001. As described above, GM6001 blocked the increases in neurite-promoting observed in cultured nerves. Gelatinolytic activity in GM6001-treated nerve explants was nearly undetectable, as shown in FIGS. 17E and 17F. Together these findings indicate that gelatinolytic activity was markedly increased by nerve explant culture and that GM6001 effectively blocked de novo MMP activity during in vitro degeneration.

EXAMPLE 16

MMP Localization in the Cultured Nerve Segments: Immunofluorescent Labeling

Figure 18A:
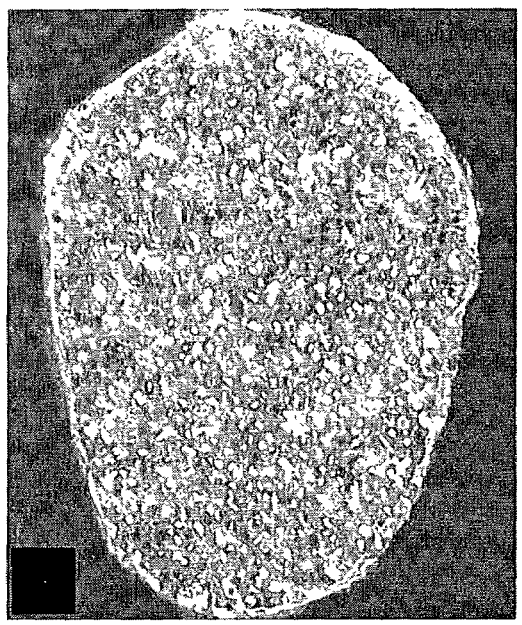
FIGS. 18A–18D show immunoexpression of MMP-2 and MMP-9 in cultured nerve explants.
Figure 18B:
Figure 18C:
Figure 18D:

The distributions of MMP-2 and MMP-9 in nerve explants cultured for 2 days were examined by immunofluorescence microscopy. MMP-2 immunolabeling of culture nerves was intense within Schwann cells and the surrounding basal laminae, as shown in FIG. 18A. Schwann cell staining with S-100 indicated that the most intense MMP-2 immunolabeling was associated with migrating Schwann cells (FIG. 18B; and see below). Also, MMP-2 immunoexpression was very similar to the pattern of gelatinolytic activity obtained by in situ zymography. On the other hand, MMP-9 immunolabeling was virtually absent within the nerve fascicles, except for rare cellular profiles. Some cellular immunoexpression of MMP-9 was seen in the surrounding epineurium, as shown in FIG. 18C. OX42 labeling was used to identify macrophages which were scattered throughout the epineurium and rarely within the nerve fascicles of cultured nerves, as shown in FIG. 18D. The compartmental distributions of MMP-9 and OX42 labeling suggested that macrophages were the main source of MMP-9. In addition, Schwann cells, and perhaps some perineurial fibroblasts, expressed MMP-2 and MMP-2 immunoreactivity was also observed diffusely in the surrounding extracellular matrix.

EXAMPLE 17

Cell Distributions and Axonal Degeneration in the Cultured Nerve Segments

After nerve injury Schwann cells become activated, dissociate their myelin and migrate extensively. S-100 immunolabeling of the cultured nerve explants showed that many Schwann cells had lost their elongated morphology and close association with axons, typical of the injury response, as shown in FIG. 18B. As expected when disconnected from the circulatory system, the number of macrophages in the nerve explants was much lower than that observed in nerve degeneration in vivo. Moreover, very few macrophages were found within the nerve fascicles and nearly all OX42-labeled cells were confined to the epineurium, as shown in FIG. 18D. It was clear that the macrophages present in the epineurial compartment at the time of nerve excision did not invade the inner nerve compartments during culture. Accordingly, the nerve explants in vitro represent a model of nerve degeneration in which the contribution of Schwann cells may be assessed independently from those of invading macrophages.

Figure 19B:
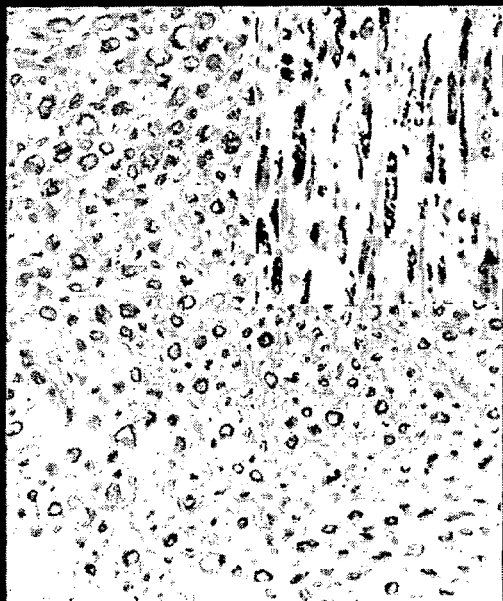
FIGS. 19A–19D show Wallerian degeneration in cultured nerve explants. The degenerative changes observed in the nerve segments cultured for 2 days were reminiscent of the initial phases of Wallerian degeneration seen in vivo.
Figure 19D:
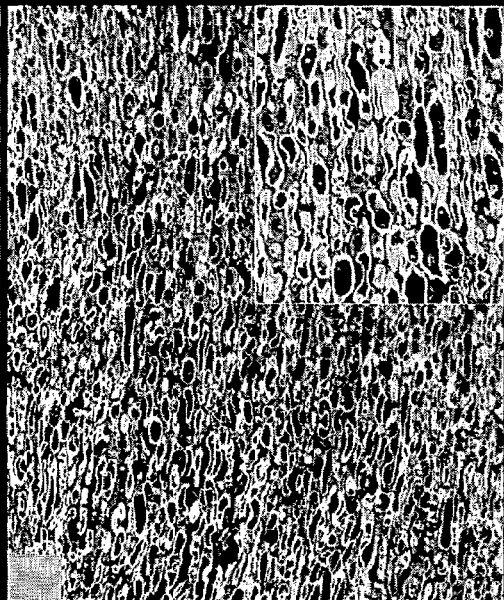
Figure 19A:
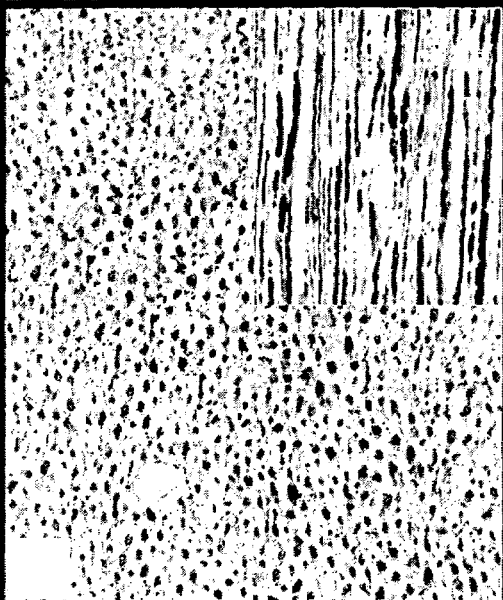
Figure 19C:
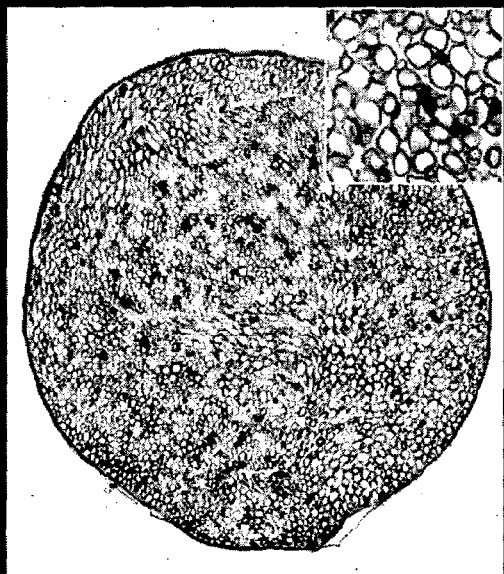

The degradation of axons was examined in cultured nerve explants by immunolabeling of neurofilaments. Results are shown in FIGS. 19A–19D. Unlike the contiguous neurofilament staining observed in normal nerve, shown in FIG. 19A, the neurofilament profiles in nerve segments cultured for 2 days were fragmented and irregular, as shown in FIG. 19B. Similar to axonal degeneration in vivo, the cultured nerves contained both annular and condensed neurofilament profiles, indicative of cytoskeleton disintegration and axonal degeneration. The degeneration of axons was especially obvious in semi-thin sections stained with toluidine blue which showed a void or a dense pellet within the residual myelin sheaths, as shown in FIG. 19D. The degenerative changes observed in the nerves cultured for 2 days were reminiscent of the initial phase of Wallerian degeneration seen in vivo (reviewed by Stoll and Muller, 1999, *Brain Pathol* 9:313–325). The main features of the secondary phase of Wallerian degeneration were also observed in cultured nerves including morphologic changes in the myelin sheath and myelin extrusion by Schwann cells, as well as Schwann cell proliferation, as shown in FIG. 19D. However, the degenerative processes resulting in further myelin degeneration (collapse and condensation) and phagocytotic removal did not occur in the 2-day nerve explant cultures. Despite the substantial degenerative alterations, the basal lamina scaffold remained structurally intact and remodeling was indicated by the high level of laminin expression by Schwann cells, as shown in FIG. 19C.

EXAMPLE 18

Cultured Nerve as Acellular Interpositional Grafts

Figure 20B:
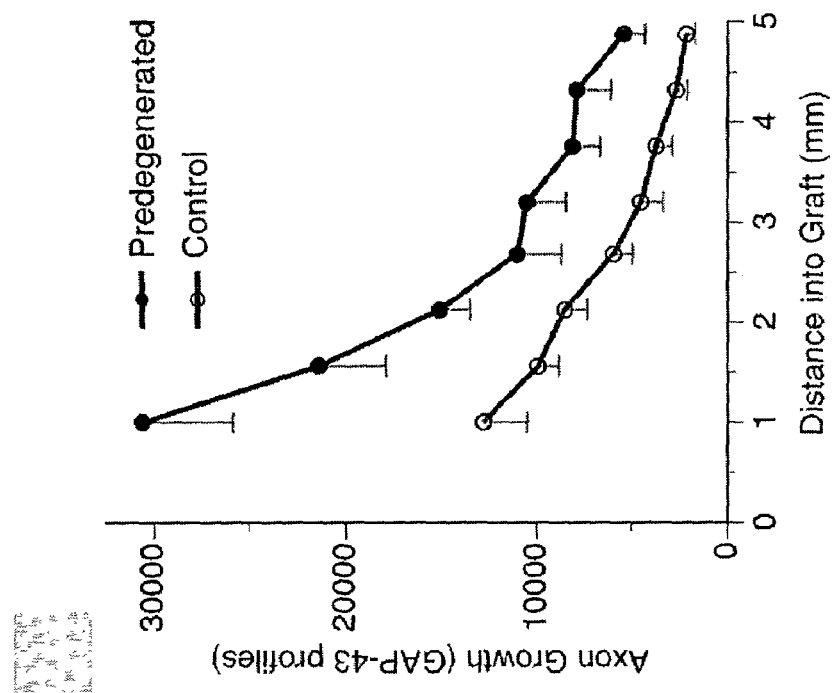
FIGS. 20A and 20B show axonal regeneration within acellular nerve grafts predegenerated in vitro. Normal and cultured (2-day, 2% serum) nerve grafts were freeze-killed, trimmed to 10 mm in length and used as interpositional grafts for the repair of transected sciatic nerves. Host rats received bilateral grafts, one normal (uncultured) and one predegenerated (cultured). Axonal regeneration was assessed after 8 days by scoring GAP-43-immunopositive profiles in transverse sections.
Figure 20A:
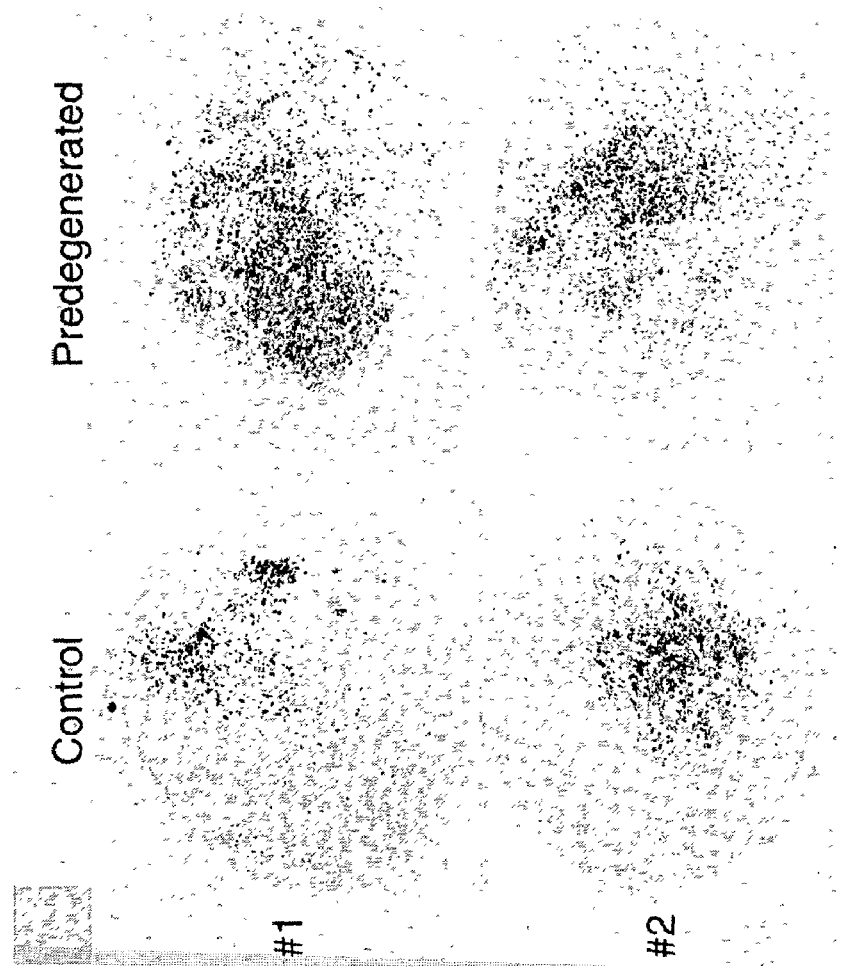

The present experiment tests the hypothesis that predegeneration in vitro improves nerve regeneration through acellular nerve allografts. Host rats received bilateral, acellular nerve grafts, one control (not predegenerated) and one predegenerated in vitro (cultured for 2-day in 2% serum). Axonal regeneration was assessed after 8 days by scoring GAP-43 immunopositive profiles in transverse sections. Axonal growth was observed in all grafts and was centrally distributed, indicating good alignment and coaptation of proximal host nerve and graft, as shown in FIGS. 20A and 20B. In 6/6 animals, the number of axons that crossed the proximal nerve-graft coaptation and entered the graft was greater in the in vitro predegenerated graft than in the contralateral control graft. On average, the score of axons within the in vitro predegenerated grafts was two-fold greater, as shown in FIG. 20B. In both graft conditions, axonal growth occurred within basal lamina tubes and was accompanied by host derived Schwann cells. These findings show that axonal regeneration into acellular nerve grafts is enhanced by in vitro predegeneration.

Degeneration increases the growth-promoting properties of denervated peripheral nerve and derivative nerve grafts. The present experiment investigated the role of MMPs in this degenerative process using a nerve explant culture model. Also, because nerve predegeneration in vivo is not feasible for the preparation of human allografts, the attributes of nerve grafts predegenerated in vitro were examined. The results of the present experiment support the following conclusions. First, early stages of Wallerian degeneration occur in short-term culture of peripheral nerve explants, despite the absence of hematogenic macrophages. The neurite-promoting activity of nerve segments is markedly increased by in vitro degeneration and to a greater extent than nerve predegenerated in vivo. The increase in neurite-promoting activity resulting from in vitro degeneration is attributed to a heightened expression and activation of MMP-2 by Schwann cells. Lastly, in vitro predegeneration enhances axonal regeneration into acellular interpositional nerve grafts.

The present experiment of peripheral nerve degeneration in vitro, finds that MMP-9 is present in trace amount mostly associated with a minor population of cells restricted to the epineurial sheath. Immunolabeling for MMP-9 is essentially absent in the endoneurial compartment of cultured nerves. In contrast, MMP-2, particularly the activated form, rapidly increases within the endoneurium in cultured nerves. Taken together with immunolocalization and in situ zymography data, the experimental data concludes that MMP-2 is expressed by Schwann cells and active enzyme is released into the surrounding endoneurium during in vitro nerve degeneration.

Combined with the present observations of nerve explants, the experimental data shows that MMP-2 represents a sufficient, if not principal, degenerative mechanism for the enhancement of the growth-promoting properties of denervated nerve (and predegenerated nerve grafts).

According to the current invention, culture of nerve explants, using conditions to support cell viability and growth, allows for cell-mediated degeneration and significantly enhances the regenerative potential of nerve grafts.

Nerve explants can be freeze-killed and stored frozen for later use as interpositional nerve grafts. Freeze-killing nerve grafts virtually eliminates the concerns of graft immunorejection. For this reason acellular nerve grafts have a greater potential for clinical applications than do cellular nerve grafts in allografting without immunosuppression.

It should be understood that the examples and embodiments described herein are for illustrative purposes only and that various modifications or changes in light thereof will be suggested to persons skilled in the art and are to be included within the spirit and purview of this application.

What is claimed is:

1. A method for promoting repair of a damaged nerve, the method comprising:
    culturing a nerve graft in vitro under predegenerating conditions that remodel the nerve graft and that increase the neurite-promoting activity of the nerve graft when subsequently implanted;
    rendering the nerve graft acellular by killing cells in the nerve graft; and
    implanting the nerve graft at a site of damage.

2. The method according to claim 1, wherein said culturing of the nerve graft in vitro is for a period of time that achieves an increase in axon ingress and extent of growth within the nerve graft when subsequently implanted.

3. The method according to claim 1, wherein the increase in neurite-promoting activity is as determined by an in vitro neurite outgrowth assay of the nerve graft.

4. The method according to claim 3, wherein the in vitro neurite outgrowth assay comprises a cryoculture assay.

5. The method according to claim 1, wherein the increase in neurite-promoting activity is as determined by an in vivo neurite outgrowth assay of the nerve graft.

6. The method according to claim 1, wherein said culturing of the nerve graft in vitro is for a period of time within the range of about 24 hours to about 96 hours.

7. The method according to claim 1, wherein said culturing of the nerve graft in vitro is for a period of time within the range of about 24 hours to about 72 hours.

8. The method according to claim 1, wherein said culturing of the nerve graft in vitro is for a period of time within the range of about 24 hours to about 48 hours.

9. The method according to claim 1, wherein said culturing of the nerve graft in vitro is conducted at a temperature within the range of about 10° C. to about 37° C. a period of time of about 48 hours.

10. The method according to claim 1, wherein said culturing of the nerve graft in vitro is conducted at a temperature within the range of about 30° C. to about 37° C.

11. The method according to claim 1, wherein said culturing of the nerve graft in vitro is conducted at a temperature of about 37° C.

12. The method according to claim 1, wherein rendering the nerve graft acellular by killing cells in the nerve graft comprises a process selected from the group consisting of freeze-killing and chemical treatment.

13. The method according to claim 1, wherein said method further comprises freezing the nerve graft for storage.

14. The method according to claim 13, wherein said freezing is carried out after said culturing in vitro.

15. The method according to claim 1, wherein said culture comprises placing the nerve graft in contact with culture medium.

16. The method according to claim 15, wherein the culture medium comprises defined medium.

17. The method according to claim 15, wherein the culture medium comprises defined medium supplemented with serum.

18. The method according to claim 15, wherein the culture medium comprises undefined medium.

19. The method according to claim 1, wherein the nerve graft is mammalian tissue.

20. The method according to claim 1, wherein the nerve graft is mammalian tissue, selected from the group consisting of human tissue, non-human primate tissue, porcine tissue, rodent tissue, and bovine tissue.

21. The method according to claim 1, wherein the nerve graft is human tissue.

22. The method according to claim 1, wherein the nerve graft comprises peripheral nerve tissue.

23. The method according to claim 1, wherein the damaged nerve comprises nerve tissue of the central nervous system.

24. The method according to claim 1, wherein said method further comprises applying a tissue adhesive to the damaged nerve, or to the nerve graft, or to both the damaged nerve and the nerve graft.

25. The method according to claim 1, wherein the nerve graft is a terminal nerve graft.

26. The method according to claim 1, wherein the nerve graft is an interpositional nerve graft.

27. The method according to claim 1, wherein said method further comprises resecting the damaged nerve prior to said implanting of the nerve graft.

28. The method according to claim 1, wherein the nerve graft is autologous with the damaged nerve.

29. The method according to claim 1, wherein the nerve graft is allogeneic with the damaged nerve.

30. The method according to claim 1, wherein the nerve graft is xenogeneic with the damaged nerve.

31. The method according to claim 1, wherein said method further comprises conducting an in vitro neurite outgrowth assay of the nerve graft after said culturing.

32. The method according to claim 31, wherein the in vitro neurite outgrowth assay comprises a cryoculture assay.

33. The method according to claim 1, wherein said method further comprises conducting an in vivo neurite outgrowth assay of the nerve graft after said culturing.

34. The method according to claim 1, wherein the nerve graft comprises peripheral nerve tissue and wherein said implanting results in axonal growth into basal lamina tubes of the nerve graft accompained by recipient-derived Schwann cells, thereby promoting repair of the damaged nerve.

35. The method according to claim 1, wherein the nerve graft comprises mammalian tissue selected from the group consisting of human tissue, porcine tissue, and bovine tissue.

36. The method according to claim 1, wherein the nerve graft comprises nerve tissue of the central nervous system.

37. The method according to claim 1, wherein the damaged nerve comprises nerve tissue of the peripheral nervous system.

38. A method for promoting repair of a damaged nerve, the method comprising:
    culturing a nerve graft in vitro under predegenerating conditions that increase the neurite-promoting activity of the nerve graft when subsequently implanted, the conditions comprising a temperature within the range of about 10° C. for a period of time within the range of about 24 hours to about 96 hours;

rendering the nerve graft acellular by killing cells in the nerve graft; and implanting the nerve graft at a site of damage.

39. The method according to claim 38, wherein said nerve graft comprises an allograft or xenograft.

40. The method according to claim 38, wherein said nerve graft comprises human tissue.

41. The method according to claim 38, wherein said nerve graft comprises procine tissue or bovine tissue.

42. The method according to claim 38, wherein said nerve graft comprises nerve tissue of the peripheral nervous system.

43. The method according to claim 38, wherein said nerve graft comprises nerve tissue of the central nervous system.

44. The method according to claim 38, wherein said nerve graft comprises nerve tissue of the peripheral nervous system.

45. The method according to claim 38, wherein said damaged nerve comprises nerve tissue of the central nervous system.

46. A method for promoting repair of a damaged nerve, the method comprising:

placing a nerve graft in conditions in vitro that are permissive to the activation and proliferation of cells within the nerve graft, are permissive to the activity of enzymes produced by cells within the nerve graft, are permissive to the degeneration and remodeling of the nerve graft in vitro, and increase the neurite-promoting activity of the nerve graft when subsequently implanted;

rendering the nerve graft acellular by killing cells in the nerve graft; and implanting the nerve graft at a site of damage.

* * * * *

UNITED STATES PATENT AND TRADEMARK OFFICE
CERTIFICATE OF CORRECTION

PATENT NO. : 6,972,168 B2 Page 1 of 1
APPLICATION NO. : 10/218864
DATED : December 6, 2005
INVENTOR(S) : Muir It is certified that error appears in the above-identified patent and that said Letters Patent is hereby corrected as shown below:

Column 26
Line 61, delete "zynography" and insert --zymography--.

Column 39
Lines 43-44, delete "within the range of about 24 hours to about 48 hours" and insert --of about 48 hours--.
Lines 47-48, delete "a period of time of about 48 hours".

Column 41
Line 1, after "10°C." and before "for a period of time" insert --to about 37°C.--.
Lines 17-18, delete "wherein said nerve graft" and insert --wherein said damaged nerve--.

Signed and Sealed this

Eighth Day of August, 2006

JON W. DUDAS
*Director of the United States Patent and Trademark Office*